(12) United States Patent
Shafren

(10) Patent No.: US 7,485,292 B2
(45) Date of Patent: Feb. 3, 2009

(54) METHOD OF TREATING A MALIGNANCY IN A SUBJECT VIA DIRECT PICORNAVIRAL-MEDIATED ONCOLYSIS

(75) Inventor: Darren R. Shafren, The Hill (AU)

(73) Assignee: Viralytics Limited, Pymble, New South Wales (AU)

( * ) Notice: Subject to any disclaimer, the term of this patent is extended or adjusted under 35 U.S.C. 154(b) by 178 days.

(21) Appl. No.: 10/539,219

(22) PCT Filed: Dec. 18, 2003

(86) PCT No.: PCT/AU03/01688

§ 371 (c)(1),
(2), (4) Date: Jan. 17, 2006

(87) PCT Pub. No.: WO2004/054613

PCT Pub. Date: Jul. 1, 2004

(65) Prior Publication Data

US 2006/0134778 A1    Jun. 22, 2006

(30) Foreign Application Priority Data

Dec. 18, 2002    (AU) .............................. 2002953436

(51) Int. Cl.
| | |
|---|---|
| A61K 39/12 | (2006.01) |
| A61K 35/76 | (2006.01) |
| A61K 35/12 | (2006.01) |
| A61K 31/7088 | (2006.01) |
| C12N 7/00 | (2006.01) |
| A61P 35/04 | (2006.01) |
| C07H 21/00 | (2006.01) |

(52) U.S. Cl. ................ 424/93.6; 424/204.1; 424/93.7; 435/235.1; 536/23.72; 514/44

(58) Field of Classification Search ................ 424/93.6; 435/320.1
See application file for complete search history.

(56) References Cited

U.S. PATENT DOCUMENTS

| | | | | |
|---|---|---|---|---|
| 5,529,774 | A | 6/1996 | Barba et al. | 424/93.21 |
| 5,585,096 | A | 12/1996 | Martuza et al. | 424/93.2 |
| 5,585,254 | A | 12/1996 | Maxwell et al. | 435/465 |
| 5,601,818 | A | 2/1997 | Freeman et al. | 424/93.21 |
| 5,674,729 | A | 10/1997 | Wimmer et al. | 435/235.1 |
| 5,681,731 | A | 10/1997 | Lebkowski et al. | 435/457 |
| 5,688,773 | A | 11/1997 | Chiocca et al. | 514/44 |
| 5,972,706 | A | 10/1999 | McCormick | 435/440 |
| 6,060,316 | A | 5/2000 | Young et al. | 435/455 |
| 6,110,461 | A | 8/2000 | Lee et al. | 424/93.6 |
| 6,136,307 | A | 10/2000 | Lee et al. | 424/93.6 |
| 6,261,555 | B1 | 7/2001 | Lee et al. | 424/93.6 |
| 6,264,940 | B1 | 7/2001 | Gromeier et al. | 424/93.2 |

FOREIGN PATENT DOCUMENTS

| | | |
|---|---|---|
| AU | 1994699487 | 11/1994 |
| AU | 1996699811 | 12/1996 |
| AU | 1998726500 | 9/1998 |
| AU | 2000776401 | 9/2000 |
| AU | 2001782402 | 4/2001 |
| AU | 2001776061 | 5/2001 |
| AU | 2001782020 | 5/2001 |
| AU | 2001770517 | 6/2001 |
| AU | 2001/784776 | 10/2001 |
| AU | 20011268146 | 12/2001 |
| AU | 2003258060 | 10/2003 |
| AU | 2004202292 | 6/2004 |
| AU | 2004203458 | 8/2004 |
| AU | 2005201079 | 4/2005 |
| CA | 2 051 289 | 3/1992 |
| EP | 1032269 | 9/2000 |
| WO | WO 90/12087 | 10/1990 |
| WO | WO 93/09221 | 5/1993 |
| WO | WO 94/18992 | 9/1994 |
| WO | WO 96/00007 | 1/1996 |
| WO | WO 99/18799 | 4/1999 |
| WO | WO 94/18992 | 9/1999 |
| WO | WO 99/45783 | 9/1999 |
| WO | WO 00/08166 | 2/2000 |
| WO | WO 00/62735 | 10/2000 |
| WO | WO 01/04334 | 1/2001 |
| WO | WO 01/12815 | 2/2001 |
| WO | WO 01/19380 | 3/2001 |

(Continued)

OTHER PUBLICATIONS

Ferdat et al. Eksp. Onkol. 1989, vol. 11, No. 5, pp. 43-48. Abstract only.*

Andreansky, et al., "The application of genetically engineered herpes simplex viruses to the treatment of experimental brain tumors." *Proc. Natl. Acad. Sci. USA* vol. 93, pp. 11313-11318 (1996).

Ansardi, et al., "RNA Replicons Derived from Poliovirus Are Directly Oncolytic for Human Tumor Cells of Diverse Origins." *Cancer Research*, vol. 61, pp. 8470-8479 (2001).

Bartolazzi, et al., "Localization of the alpha 3 beta 1 Integrin in Some Common Epithelial Tumors of the Ovary and in Normal Equivalents." *AntiCancer Research*, 13:1-12 (1993).

Bergelson, et al., "The Integrin VLA-2 Binds Echovirus 1 and Extracellular Matrix Ligands by Different Mechanisms." *J. Clin. Invest.*, vol. 92, pp. 232-239 (1993).

(Continued)

*Primary Examiner*—Bruce Campell
*Assistant Examiner*—Bao Qun Li
(74) *Attorney, Agent, or Firm*—DLA Piper LLP (US)

(57) ABSTRACT

There are provided methods for treatment of abnormal cells such as cancer cells in a mammal. The methods involve treating the mammal with virus selected from echoviruses and modified forms and combination thereof, which recognize $\alpha_2\beta_1$ for infectivity of the cells. There are also provided methods for screening viruses for use in a method of the invention as well as pharmaceutical compositions for use in the methods.

27 Claims, 19 Drawing Sheets

FOREIGN PATENT DOCUMENTS

| | | |
|---|---|---|
| WO | WO 01/53506 | 7/2001 |
| WO | WO 02/43647 | 6/2002 |
| WO | WO 02/50304 | 6/2002 |
| WO | WO 02/087625 | 11/2002 |
| WO | WO 02/091997 | 11/2002 |
| WO | WO 02/092826 | 11/2002 |
| WO | WO 03/008586 | 1/2003 |
| WO | WO 03/010306 | 2/2003 |
| WO | WO 03/073918 | 9/2003 |
| WO | WO 03/082200 | 10/2003 |
| WO | WO 03/092579 | 11/2003 |
| WO | WO 03/094938 | 11/2003 |
| WO | WO 2004/003562 | 1/2004 |
| WO | WO 2004/054613 | 7/2004 |
| WO | WO 2005/002607 | 1/2005 |
| WO | WO 2005/007824 | 1/2005 |
| WO | WO 2005/030139 | 4/2005 |
| WO | WO 2005/087931 | 9/2005 |
| WO | WO 2005/107474 | 11/2005 |
| WO | WO 2006/002394 | 1/2006 |
| WO | WO 2006/047301 | 5/2006 |

OTHER PUBLICATIONS

Cannistra, et al., "Expression and Function of beta 1 and alpha v beta 3 Integrins in Ovarian Cancer." *Gynecologic Oncology*, vol. 58, pp. 216-225 (1995).

Cardarelli, et al., "The Collagen Receptor alpha 2 beta 1, from MG-63 and HT1080 Cells, Interacts with a Cyclic RGD Peptide." *The Journal of Biological Chemistry*, vol. 267, No. 32, pp. 23159-23164 (1992).

Casey, et al., "Beta 1-Integrins Regulate the Formation and Adhesion of Ovarian Carcinoma Multicellular Spheriods," *American Journal of Pathology*, vol. 159, No. 6, pp. 2071-2080 (2001).

Chan, et al., "In Vitro and in Vivo Consequences of VLA-2 Expression on Rhabdomyosarcoma Cells." *Science*, vol. 251, pp. 1600-1602 (1991).

Frankel, et al., "Abrogation of Taxol-induced $G_2$-M Arrest and Apoptosis in Human Ovarian Cancer Cells Grown as Multicellular Tumor Spheriods." *Cancer Research*, vol. 57, pp. 2388-2393 (1997).

He, et al., "A simplified system for generating recombinant adenoviruses." *Proc. Natl. Acad. Sci. USA*, vol. 95, pp. 2509-2514 (1998).

Kamata, Tetsuji and Takada, Yoshikazu, "Direct Binding of Collagen to the I Domain of Integrin $\alpha 2\beta 1$ (VLA-2, CD49b/CD29) in a Divalent Cation-independent Manner." *The Journal of Biological Chemistry*, vol. 269, pp. 26006-26010 (1994).

Kramer, Randall H. and Marks, Nancy, "Identification of Integrin Collagen Receptors on Human Melanoma Cells." *The Journal of Biological Chemistry*, vol. 264, No. 8, pp. 4684-4688 (1988).

Moser, et al., "Evidence for Preferential Adhesion of Ovarian Epithelial Carcinoma Cells to Type I Collagen Mediated by the $\alpha 2\beta 1$ Integrin." *Int. J. Cancer*, vol. 67, pp. 695-701 (1996).

Natali, et al., "Clinical Significance of $\alpha_v \beta_3$ Integrin and Intercellular Adhesion Molecule-1 Expression in Cutaneous Malignant Melanoma Lesions." *Cancer Research*, vol. 57, pp. 1554-1560 (1997).

Nemunaitis, John, "Oncolytic viruses." *Investigational New Drugs*, vol. 17, pp. 375-386 (1999).

Pietiäinen, Vilja, "Effects of echovirus 1 Infection on Cellular Gene Expression." *Virology*, vol. 276, pp. 243-250 (2000).

Pevear, et al., "Activity of Pleconaril against Enteroviruses." *Antimicrobiol Agents and Chemotherapy*, vol. 43, No. 9, pp. 2109-2115 (1999).

Ramos, et al., "Analysis of Integrin Receptors for Laminin and Type IV Collagen on Metastatic B16 Melanoma Cells." *Cancer Research*, vol. 50, pp. 728-734 (1990).

Randazzo, et al., "Treatment of Experimental Intracranial Murine Melanoma with a Neuroattenuated Herpes Simplex Virus 1 Mutant." *Virology*, vol. 211, pp. 94-101 (1995).

Rossman, et al., "Cell Recognition and Entry by Rhino- and Enteroviruses." *Virology*, vol. 269, pp. 239-247 (2000).

Satyamoorthy, et al., "Adenovirus Infection Enhances Killing of Melanoma Cells by a Mitotoxin.", *Cancer Research*, vol. 57, pp. 1873-1876 (1997).

Shafren, et al., "Coxsackievirus A21 Binds to Decay-Accelerating Factor but Requires Intercellular Adhesion Molecule 1 for Cell Entry." *Journal of Virology*, vol. 71, No. 6, pp. 4736-4743 (1997).

Strong, et al., "The molecular basis of viral oncolysis: usurpation of the Ras signaling pathway by reovirus," *The EMBO Journal*, vol. 17, No. 12, pp. 3351-3362 (1998).

Tsao, et al., "Characterization of Human Ovarian Surface Epithelial Cells Immortalized by Human Papilloma Viral Oncogenes (HPV-E6E7 ORFs)." *Experimental Cell Research*, vol. 218, pp. 499-507 (1995).

Xiao, et al., "Interaction of Coxsackievirus A21 with Its Cellular Receptor, ICAM-1." *Journal of Virology*, vol. 75, No. 5, pp. 2444-2451 (2001).

Xing, Li, "Non-enveloped Virus Infection Probed with Host Cellular Molecules: A Structural Study." Centre for Biotechnology, Department of Biosciences at Novum, Karolinska Institutet, Sweden: Stockholm 2002.

Anastassiou, G. et al. "Expression of VLA-2, VLA-3 and $a_v$ integrin receptors in ureal melanoma: association with microvascular architecture of the tumour and prognostic value". *Br. J. Ophthalmol.* 2000; 84:899-902.

Casasnovas, J.M. and Springer, T.A. "Pathway of Rhinovirus disruption by soluble intercellular adhesion molecule 1 (ICAM-1): an intermediate in which ICAM-I is bound and RNA is released" *Journal of Virology* 1994; vol. 68(9): 5882-5889.

Daraï, E. et al "Soluble adhesion molecule in serum and cyst fluid from patients with cystic tumours of the ovary", *Human Reproduction*, 13(10):2831-2835, 1998.

DeTulleo, L. and Kirchhausen, T. "The clathrin endocytic pathway in viral infection", *The EMBO Journal*, 17 (16): 4585-4593, 1998.

Fiucci, G. et al "Caveolin-1 inhibits anchorage-independent growth, anoikis and invasiveness in MCF-7 human breast cancer cells" *Oncogene* (2002) 21: 2365-2375.

Greve, J.M. et al. "Mechanisms of receptor-mediated Rhinovirus neutralization defined by two soluble forms of ICAM-1", *Journal of Virlogy*, 1991, 65(11):6015-6023.

Kang, X. et al "Clinical evaluation of serum concentrations of intercellular adhesion molecule-1 in patients with colorectal cancer" *World Journal of Gastroenterology* 2005; 11(27):4250-4253.

Lonberg-Holm, K., et al "Unrelated animal viruses share receptors" *Nature* 1976, 259:679-681.

Marjomäki, V., et al "Internalization of Echovirus 1 in Caveolae" *Journal of Virology*, 2002, 76(4):1856-1865.

Martin, S. et al "Efficient neutralization and disruption of Rhinovirus by chimeric ICAM-1/Imnmunoglobulin molecules", *Journal of Virology*, 1993, 67(6):3561-3568.

Nasu, K. et al "Serum levels of soluble intercellular adhesion molecule-1 (ICAM-1) and the expression of ICAM-1 mRNA in uterine cervical cancer" 1997 *Gynecol. Oncol.* vol. 65(2): 304-308.

Newcombe, N.G. et al. "Enterovirus capsid interactions with decay-accelerating factor mediate lytic cell infection"*Journal of Virology*, 2004, 78(3):1431-1439.

Newcombe, N.G. et al. "Cellular receptor interactions of the C-cluster human group A coxsackieviruses" *Journal of General Virology*, 2003, 84:3041-3050.

Pui, C.H. et al "Serum intercellular adhesion molecule-1 in childhood malignancy" *Blood*, 82(3):895-898, 1993.

Schaefer, M. et al, "Correlation between sICAM-1 and depressive symptoms during adjuvant treatment of melanoma with interferon-alpha" *Brain Behav. Immuno* 2004, 18(6): 555-562.

Shafren, D.R. et al "Antibody binding to individual short consensus repeats of decay-accelerating factor enhances Enterovirus cell attachment and infectivity". *The Journal of Immunology* 1998, 160:2318-2323.

Shafren, D. R. et al "Cytoplasmic interations between decay-accelerating factor and intercellular adhesion molecule-1 are not required for coxsackievirus A21 cell infection," *Journal of General Virology* 2000, 81:889-894.

Taguchi, O. et al "Circulating intercellular adhesion molecule-1 in patients with lung cancer" 1997 *Intern. Med.* vol. 36(1): 14-18.

Triantafilou, M. et al "Identification of Echovirus 1 and Coxsackievirus A9 receptor molecules via a nosed flow cytometric quantification method" *Cytometry* 43:279-289 (2001).

van den Engel, N.K. et al "Oral DNA vaccination with a plasmid encoding soluble ICAM-1 modulates cytokine expression profiles in nonobese diabetic mice". *J. Mol. Med.* May, 2002; 80(5): 301-308.

* cited by examiner

OVCA-

OVHS-1

OWA-42

SKOV-3

CONTROL CELLS          EV1 INFECTION

A

B

A

B

METHOD OF TREATING A MALIGNANCY IN A SUBJECT VIA DIRECT PICORNAVIRAL-MEDIATED ONCOLYSIS

CROSS REFERENCE TO RELATED APPLICATIONS

This application claims the benefit of priority under 35 USC § 365(c) of International Application No. PCT/AU2003/001688, with an international filing date of 18 Dec. 2003, which claims priority to Australian Patent Application No. 2002953436 filed 18 Dec. 2002, which are incorporated herein by reference in their entirety.

FIELD OF THE INVENTION

The present invention relater to the killing of abnormal cells utilising a virus. There is also described a method of screening cells to ascertain whether they are susceptible to treatment with virus, as well as pharmaceutical compositions. The invention finds veterinary as well as broad application in the human medical field.

BACKGROUND OF THE INVENTION

Ovarian cancer is a leading cause of morbidity in the female population. Several malignancies arise from the ovary. Epithelial carcinoma of the ovary is one of the most common gynaecologic malignancies and the fifth most frequent cause of cancer death in women, with half of all cases occurring in women over age 65.

Approximately 5% to 10% of ovarian cancers are familial and 3 distinct hereditary patterns have been identified: ovarian cancer alone, ovarian and breast cancers, or ovarian and colon cancers. The most important risk factor for ovarian cancer is a family history of a first-degree relative (mother, daughter, or sister) with the disease. The highest risk appears in women with 2 or more first-degree relatives with ovarian cancer. The risk is somewhat less for women with one first-degree and one second-degree (grandmother, aunt) relative with ovarian cancer. In most families affected with breast and ovarian cancer syndrome or site-specific ovarian cancer, genetic linkage has been found to the BRCA1 locus on chromosome 17q21. BRCA2, also responsible for some instances of inherited ovarian and breast cancer, has been mapped by genetic linkage to chromosome 13q12.

The lifetime risk for developing ovarian cancer in patients harbouring germ-line mutations in BRCA1 is substantially increased over the general population. Two retrospective studies of patients with germ-line mutations in BRCA1 suggest that these women have improved survival compared to BRCA1 negative women. When interpreting this data, it must be considered that the majority of women with a BRCA1 mutation probably have family members with a history of ovarian and/or breast cancer. Therefore, these women may have been more vigilant and inclined to participate in cancer screening programs that may have led to earlier detection. For patients at increased risk, prophylactic oophorectomy may be considered after the age of 35 if childbearing is complete. However, the benefit of prophylactic oophorectomy has not yet been established. A small percentage of women may develop a primary peritoneal carcinoma, similar in appearance to ovarian cancer, after prophylactic oophorectomy (Xiao, C. et al., 2001). Epithelial carcinomas are the most common types of ovarian cancer. Stromal and germ cell tumors are relatively uncommon and comprise less than 10% of cases.

Ovarian cancer usually spreads via local shedding into the peritoneal cavity followed by implantation on the peritoneum, and via local invasion of the bowel and the bladder. The highly lethal nature of this tumor is due to the absence of symptoms in women with early stages of this disease. The incidence of positive nodes at primary surgery has been reported as high as 24% in patients with stage I disease, 50% in patient with stage II disease, 74% in patients with stage III disease, and 73% in patients with stage IV disease. Tumor cells may also block diaphragmatic lymphatics. The resulting impairment of lymphatic drainage of the peritoneum is thought to play a role in development of ascites in ovarian cancer. Also, transdiaphragmatic spread to the pleura is common.

Prognosis in ovarian cancer is influenced by several factors, but multivariate analyses suggest that the most important favorable factors include younger age, good performance status, cell type other than mucinous and clear cell, lower stage, well differentiated tumor, smaller disease volume prior to any surgical debulking, absence of ascites, and smaller residual tumor following primary cytoreductive surgery. For patients with stage I disease, the most important prognostic factor is grade, followed by dense adherence and large-volume ascites. DNA flow cytometric analysis of stage I and stage IIA patents may identify a group of high-risk patients. Patients with clear cell histology appear to have a worse prognosis. Patients with a significant component of transitional cell carcinoma appear to have a better prognosis.

Although the ovarian cancer-associated antigen, CA 125, has no prognostic significance when measured at the time of diagnosis, it has a high correlation with survival when measured one month after the third course of chemotherapy for patients with stage III or stage IV disease (Rossmann, M. G. et al., 2000). For patients whose elevated CA 125 normalizes with chemotherapy, more than one subsequent elevated CA 125 is highly predictive of active disease, but this does not mandate immediate therapy.

Most patients have widespread disease at the time of diagnosis because ovarian cancer is often asymptomatic in its early stages. Partly as a result of this, yearly mortality in ovarian cancer is approximately 65% of the incidence rate. Long-term follow-up of suboptimally debulked stage III and stage IV patients reveals a 5-year survival rate of less than 10% even with platinum-based combination therapy. Nevertheless, early stages of the disease are curable in a high percentage of patients.

At present the treatment for late stage ovarian cancers involves a total abdominal hysterectomy, careful examination of serosal surfaces, and attempts to debulk all gross disease usually followed by combination chemotherapy that includes a platinum analogue. The survival rate is then between six to forty month, long term survival being less than ten percent.

There has been ongoing research with the aim of identifying molecules that are differentially expressed in benign and malignant ovarian tumors.

Ovarian carcinomas have been found to express the integrin $\alpha_2\beta_1$ (Moser, T. L. et al., 1996; Cannistra, S. A. et al., 1995; Bartolazzi, A. et al., 1993). $\alpha_2\beta_1$ promotes metastatic dissemination of human ovarian epithelial carcinoma via specific binding interactions with type 1 collagen (Schiro, J. A. et al., 1991; Cardarelli, P. M. et al., 1992). Up-regulated surface-expression of integrin $\alpha_2\beta_1$ has also previously been observed on human gastric carcinoma.

The interaction of $\alpha_2\beta_1$ with type 1 collagen likely plays a critical role in peritoneal seeding as well as in metastasis, and over expression of $\alpha_2\beta_1$ has been shown to induce metastatic properties in non-metastatic cells (Chan, B. M. et al., 1991).

Blocking of $\alpha_2\beta_1$ has been shown to largely inhibit adhesion of ovarian carcinomas by type 1 collagen.

Viruses capable of inducing lysis of malignant cells through their replication process are known as oncolytic viruses. Most oncolytic viruses require proliferation in the same species or cell lineage. Infection of a cell by a virus involves attachment and uptake into the cell which leads to or is coincidental with uncoating of the viral capsid, and subsequently replication within the cell.

Oncolytic viruses assessed for capacity to kill cancer cells have included the adenovirus subtype Egypt 101 virus which showed oncolytic activity in the HeLa uterine/cervix cancer cell line, mumps virus for treatment of gastric carcinoma, uterine carcinoma and cutaneous carcinoma, Newcastle Disease Virus (NDV), influenza virus for treatment of ovarian cancer, and adenovirus for treatment of cervical carcinoma (Nemunaitis J; 1999).

Other reports have indicated that adenoviruses and attenuated poliovirus recombinants may have use in the treatment of malignant glioma cells (e.g. Andreansky S. S., 1996), and that reovirus shows lytic capability in human U87 glioblastoma cells and NIH-3T3 cells with an activated Ras signalling pathway (e.g. Strong J. E. et al, 1998).

A vaccinia oncolysate has also been used in clinical trials to treat melanoma (Stage II) patients (Nemunaitis J., 1999). Modified, non-neurovirulent Herpes simplex viruses (HSV) have been reported as showing promise for the treatment of brain tumors including intracranial melanoma, and subcutaneous human melanoma (Randazzo B. R., 1997), while adenovirus infection has been reported to enhance killing of melanoma cells by the plant mitotoxin, saporin (Satyamoorthy K., 1997).

The receptor on target cells recognised by adenovirus differs for different adenovirus types. That is, adenovirus subgroups A, C, D, E and F for instance recognise the CAR receptor while Adenovirus type 5 (subgroup C), Adenovirus type 2 (subgroup C) and Adenovirus type 9 (subgroup D) recognise major histocompatibility class II molecule, $\alpha_m\beta_2$ and $\alpha_v$ integrins, respectively. The CAR receptor is known to be expressed on melanoma cell lines.

Heparan sulfate is recognised by Herpes simplex types 1 and 2 and human herpes virus 7, Adeno-associated virus type 2. The receptor for human Herpesvirus 7 is CD4 while Epstein-Barr virus recognises complement receptor Cr2 (CD21). Poliovirus type 1 and 2 recognise poliovirus receptor (Pvr) for cell adhesion while reovirus recognises sialic acid. Influenza A and B virus recognise the sialic acid N-acetyl neuraminic acid for cell adhesion In contrast, influenza type C virus recognises the sialic acid 9-O-acetyl neuraminic acid. Vaccina virus recognises both epidermal growth factor receptor and heparan sulfate. Coxsackievirus A13, A15, A18 and A21 recognise ICAM-1 and the complement regulatory protein DAF (CD55) (see eg. Shafren D. R., et al 1997). International Patent Application No. PCT/AU00/01461 describes the administration of Coxsackievirus which recognises ICAM-1 for cell infectivity to a subject for lysis of melanoma cells express ICAM-1. DAF is also recognised by Enterovirus 70 (see eg. Flint S J, et al (2000) Principles of Virology: molecular biology, pathogenesis and control, ASM Press, Washington).

A study evaluating the adaptability of ovarian cells to subculture and their potential use for the detection of viruses has been reported (Harris, R E and Pindak, F F, 1975). In the study, normal ovarian cell cultures were challenged with a broad range of viruses including Picornavirus such as Coxsackievirus A, Coxsackievirus B, Poliovirus, Echovirus and Cardiovirus and serotypes thereof,; Paramyxovirus such as Newcastle disease virus, Measles virus, distemper virus; Adenovirus human subgroup serotypes 3, 4, 7 and 21; Herpes simplex virus, Type 1; Togavirus such as Sindbis and Mararo; Reovirus serotypes 1 to 3; and Vaccinia virus. The study demonstrated that cells from human ovaries can be grown long-term in cell culture and may be passaged an undetermined number of times for the propagation of various vises in vitro and proposed that such cultures may be useful for the purpose of studying viral pathogenisis and pathology of viral infection. The report further suggested that as some viruses such as poliovirus and vaccinia have been shown to cross the human placenta and infect the fetus, the study of viral interactions with normal ovarian cells in culture may be a means of furthering teratogenic investigations.

Metastatic tumor spread is a pathological process associated with a series of adhesion/de-adhesion events coupled with regulated tissue degradation. Adhesion to and migration through the extracellular matrix is essential for tumor invasion. Despite progress being made in the treatment of malignancies, the treatment of cancer including ovarian malignancies presents a major challenge for research and there remains a need for alternatives to existing therapy approaches.

SUMMARY OF THE INVENTION

The present invention relates to the observation that significant killing of abnormal cells such as cancer cells expressing the integrin $\alpha_2\beta_1$ may be achieved utilising echovirus which recognises $\alpha_2\beta_1$ for cell infectivity.

Accordingly, in an aspect of the present invention there is provided a method for treatment of abnormal cells in a manual, comprising treating the mammal with an effective amount of virus selected from echoviruses, and modified forms and combinations thereof, which recognise $\alpha_2\beta_1$ for infectivity of the cells such that at least some of the cells are killed by the virus.

A single virus serotype which recognises $\alpha_2\beta_1$ may be administered to the mammal or a plurality of different echoviruses which recognise $\alpha_2\beta_1$ may be administered.

The term "abnormal cells" for the purpose of the present invention is to be taken in a broadest sense to include malignant cells, the cells of any abnormal growth, and any cells having abnormal upregulated expression of integrin $\alpha_2\beta_1$ relative to corresponding normal cells of the same cell type expressing their normal phenotype, whether the cells are cancer cells or not and whether the cells proliferate at an abnormal rate or not. Accordingly, the term encompasses pre-neoplastic and neoplastic cells, and cells that may or may not ultimately develop into cancer cells. An abnormal growth may for instance be a benign or malignant tumor. The abnormal cells will usually be malignant cells. Generally, the abnormal cells will have upregulated expression of $\alpha_2\beta_1$ compared to surrounding tissue in which the abnormal cells are found. Hence, the virus will typically preferentially infect the abnormal cells due to the greater likelihood of contacting $\alpha_2\beta_1$ on those cells. As such, the virus may be used to effectively target the abnormal cells.

A method of the invention is particularly suitable for treating ovarian cancer in a patient or cancer that has metastasised from a primary ovarian tumor. However, the invention is not limited to the treatment of such cancers and methods described herein find application in the treatment of other cancers including melanoma and prostate tumors as well as breast cancer, colon cancer, colorectal cancer, and secondary cancers that have spread therefrom to other sites in the body. For instance, the virus may be administered to melanoma cancer cells in areas of the body other than the skin of the mammal. Accordingly, methods of the invention extend to the treatment of a malignancy where the malignancy has metastisised to a site or tissue in the mammal not normally associated with infection by echoviruses.

Typically, the virus will be administered to the mammal as live, complete virus. Alternatively, nucleic acid encoding the viral genome or sufficient thereof for generation of the virus may for instance be administered for uptake by the cells and generation of live, complete virus within the cells. The nucleic acid may comprise a single RNA or DNA molecule or a plurality of such molecules encoding different ones of the viral proteins, respectively.

The virus may also be used to screen abnormal cells to ascertain for instance whether the virus may be suitable for treating the mammal from which the cells were obtained or whether a different treatment protocol not involving the virus may be more beneficial. Conversely, different echoviruses and/or modified forms or combinations thereof may be screened using samples of cells taken from the mammal in order to select the most appropriate virus for treating the mammal.

Accordingly, in another aspect of the invention there is provided a method of screening a sample of abnormal cells from a mammal for susceptibility to virus induced cell death to evaluate administering virus to the mammal for treatment of the abnormal cells, the method comprising the steps of:
(a) providing the sample of the abnormal cells from the mammal;
(b) treating the cells with the virus for a period of time sufficient to allow infection of the cells by the virus; and
(c) determining whether the virus has infected and caused death of at least some of the abnormal cells;

wherein the virus is selected from echoviruses, and modified forms and combinations thereof, which recognise $\alpha_2\beta_1$ for infectivity of the abnormal cells.

A virus may also be selected for use in a method of the invention by testing whether a given virus is capable of infecting and killing at least some of the abnormal cells in the sample. In particular, the testing may involve screening a number of different viruses by incubating each virus with a sample of the abnormal cells respectively, and determining whether the cells are killed as a result of infection by the virus.

Hence, in still another aspect of the invention there is provided a method of screening a virus for ability to infect and cause death of abnormal cells from a mammal to evaluate administering the virus to the mammal for treatment of the abnormal cells, the method comprising the steps of:
(a) selecting the virus;
(b) treating a sample of the abnormal cells from the mammal with the virus for a period of time sufficient to allow infection of the cells by the virus; and
(c) determining whether the virus has infected and caused death of at least some of the abnormal cells;

wherein the virus is selected from echoviruses, and modified forms and combinations thereof, which recognise $\alpha_2\beta_1$ for infectivity of the abnormal cells.

The method may also comprise the step of comparing the ability of the selected virus to infect and cause the death of the cells with that of another echovirus or modified form thereof subjected to steps (b) and (c) utilising another sample of the cells and which recognises $\alpha_2\beta_1$ for cell infectivity.

Death of the cells will typically result from infection of the cells by the virus, and may be caused by either lysis of the cells due to intracellular replication of the virus or by infection triggering apoptosis most likely as a result of the activation of cellular caspases. Once lysed, the cytosolic contents of infected cells may spill from the ruptured plasma membranes, and antigens including cell surface antigens capable of eliciting an immune response to the abnormal cells may be released. Hence, treatment of abnormal cells in a mammal in accordance with a method of the invention may provide a boost to the immunity of the mammal against the abnormal cells.

Accordingly, in another aspect of the invention there is provided a method for inducing an immune response in a mammal against abnormal cells expressing $\alpha_2\beta_1$, the method comprising infecting abnormal cells in the mammal with virus selected from echoviruses, modified forms and combinations thereof, which recognise $\alpha_2\beta_1$ for infectivity of the abnormal cells and wherein lysis of at least some of cells is caused.

Generally, the virus will be provided in the form of a pharmaceutical composition for use in a method of the invention. As such, in a yet further aspect there is provided a pharmaceutical composition for treating abnormal cells in a mammal, comprising an inoculant for generating virus to treat the cells such that at least some of the cells are killed by the virus together with a pharmaceutically acceptable carrier, wherein the virus is selected from echoviruses, and modified forms and combinations thereof, which recognise $\alpha_2\beta_1$ for infectivity of the cells.

In another aspect of the present invention there is provided the use of an inoculant for generating virus in the manufacture of a medicament for treating abnormal cells in a mammal with the virus such that at least some of the abnormal cells are killed wherein the virus is selected from echovirus, and modified forms and combinations thereof, which recognise $\alpha_2\beta_1$ for infectivity of the abnormal cells.

In still another aspect of the invention there is provided the use of an inoculant for generating virus in the manufacture of medicament for inducing an immune response against abnormal cells in a mammal, where the virus is selected from echovirus, and modified forms and combinations thereof, which recognise $\alpha_2\beta_1$ for infectivity of the abnormal cells and kill the cells.

Typically, an echovirus utilised in accordance with a method of the invention will be an echovirus selected from the group consisting of Echovirus EV1, Echovirus EV8 and Echovirus EV22. While the virus will usually be a common animal echovirus, the invention is not limited thereto and a recombinant virus engineered to be capable of infecting and killing the abnormal cells, or a virus that for instance has otherwise been modified to enhance its ability to infect and kill the cells, may be utilised.

The same virus may be administered to the mammal during different treatment courses. Preferably, however, different viruses are used for different treatment courses to avoid or lessen the potential effect of any immune response to the previous virus administered. A virus may for instance be administered topically, intratumorally or systemically to the mammal.

The mammal may be any mammal in need of treatment in accordance with the invention. Typically, the mammal will be a human being.

A method of the invention may be used as an adjunct to another treatment of the abnormal cells such as a conventional cancer treatment, or as a treatment in the absence of other therapeutic treatments. In particular, a method of the invention may be utilised where conventional treatment is not suitable or practical, or in the instance where excision of abnormal cells may leave scaring or disfigurement which is unacceptable to the patient, particularly from the patient's face such as from their nose or lip. The virus may be administered to the patient prior to and/or after excision of the abnormal cells. Administration after excision may kill residual abnormal cells left in the surrounding tissue.

Accordingly, one or more embodiments of the invention provide an alternative therapeutic treatment that may be used both following diagnosis of early stage and latter stage malignancy, and which further find application in the killing of abnormal cells prior to and remaining after surgery. Using protocols as described herein the skilled addressee will be able to readily select a suitable virus for use in the methods of the invention, and determine which abnormal cells are susceptible to infection leading to the death of the cells.

In still another aspect of the present invention there is provided an applicator for applying an inoculant to a mammal for generating virus to treat abnormal cells in the mammal, wherein the applicator comprises a region impregnated with the inoculant mammal such that the inoculant is in contact with the mammal, and the virus is selected from echoviruses, and modified forms and combinations thereof, which recognise $\alpha_2\beta_1$ for infectivity of the cells.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed anywhere before the priority date of each claim of this application.

The features and advantages of the invention will become further apparent from the following description of preferred embodiments of the invention.

DETAILED DESCRIPTION OF PREFERRED EMBODIMENTS OF THE INVENTION

Figure 1:
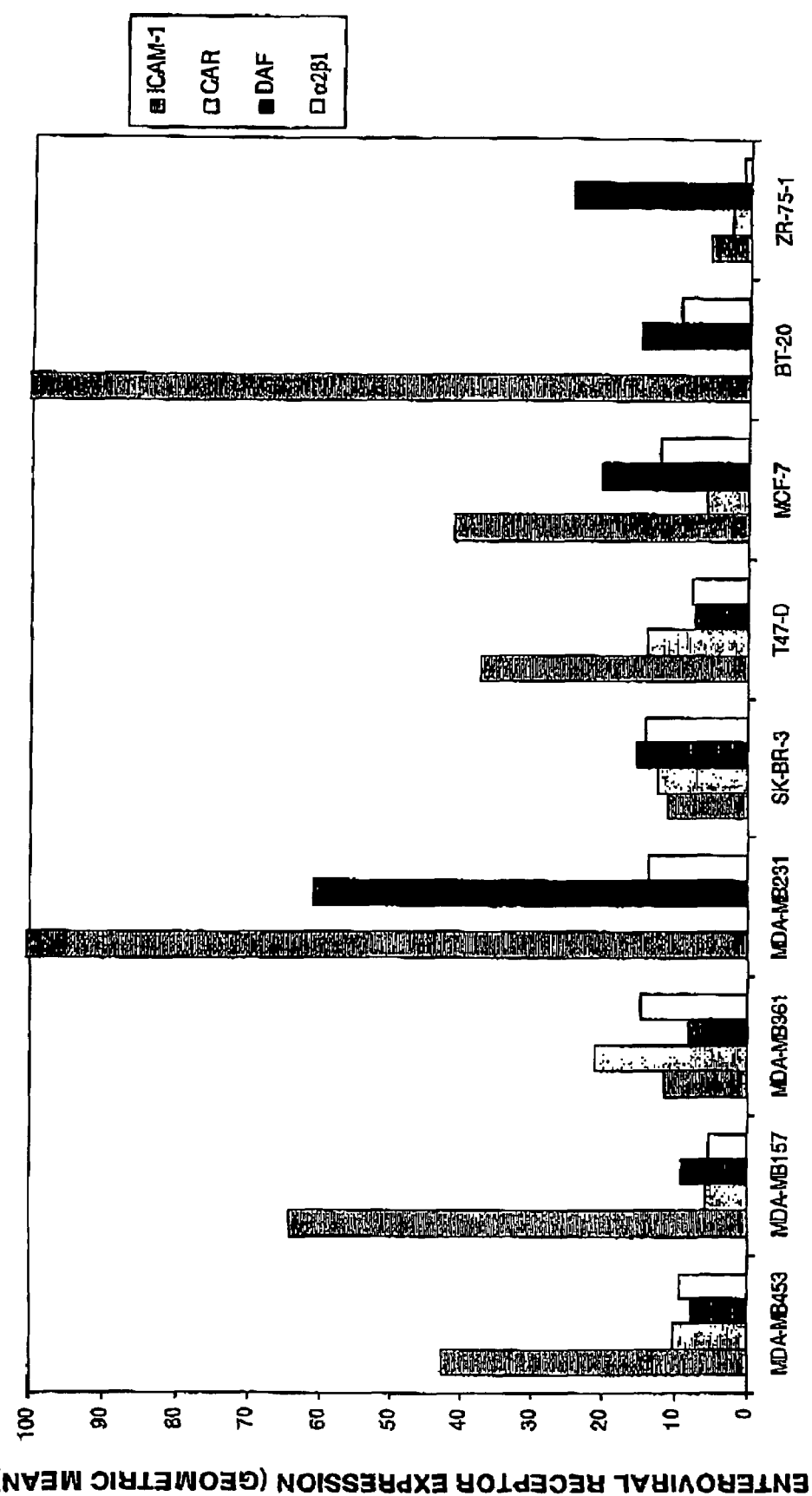
FIG. 1 shows flow cytometric analysis of the levels of surface expressed ICAM-1, CAR, DAF and $\alpha_2\beta_1$ on the surface of breast cancer cell. The breast cancer cells were incubated with R-phycoerythrin-conjugated F(ab')$_2$ fragment of goat anti-mouse immunoglobulin in the presence or absence of corresponding monoclonal antibodies specific for these receptors. The geometric mean of the conjugate sample was subtracted from the geometric mean of the enterovirus receptor sample revealing the relative level of expression of the receptor.

To determine whether a virus is capable of infecting and causing death of cells of a tumor, a biopsy may be taken from the tumor and a preparation of cells prepared using conventional techniques prior to: (i) confirming virus receptor cell surface expression and (ii) challenging the cells with the virus and monitoring the cells for infection and cell death over a predetermined incubation period, typically about 2 days although this may vary depending on the virus used. Expression of $\alpha_2\beta_1$ may be readily confirmed by flow cytometric analysis. A number of viruses may be screened in this way simultaneously utilising different aliquot's of the prepared malignant cells, the virus showing the greater degree of infectivity and cell death may then be selected for administration to the subject from whom the biopsy was taken. Similarly, different malignant cell preparations from biopsies taken from different sources may be employed in an assay using a specific virus. The biopsies may be taken from different sites of a single individual or from a number of individuals.

A virus used in a method as described herein will desirably cause few or only minor clinical symptoms in the recipient. Such viruses are readily obtainable from commercial sources well known to the skilled addressee and can be screened for their effectiveness in the instant methods in the manner described above. Desirably, the virus will normally be an echovirus selected from the group consisting of Echovirus EV1, Echovirus EV7, Echovirus EV8 and Echovirus EV22. Each of these viruses recognise $\alpha_2\beta_1$ for cell infectivity. EV1 has for instance been associated with mild upper respiratory illnesses and also pleurodynia (Fields B. N. et al, 2000; McCracken A. W. et al, 1969).

The expression of $\alpha_2\beta_1$ is believed to be upregulated on ovarian carcinomas due to the prevalent collagen I matrix it encounters in the mesothelial. Numerous malignant melanomas have also been shown to express upregulated levels of $\alpha_2\beta_1$ (Kramer R. H. and Marks N, 1989; Ramos D. M. et al, 1990). EV1 and collagen attach to $\alpha_2\beta_1$ using different residues in domain I of the $\alpha_2\beta_1$ subunit (Bergelson J. H., 1993). The itegrin $\alpha_2\beta_1$ cannot simultaneously accommodate EV1 and collagen. However, the virus binds $\alpha_2\beta_1$ with a 10-fold increase in affinity compared to collagen I (Xing L, 2002).

For the purpose of screening a given virus to ascertain whether it is capable of infecting and causing the death of malignant cells, malignant cell lines may be used rather than primary malignant cells isolated from a biopsy.

The selected virus will preferably be injected directly into a number of sites on a malignant tumor in order to maximise the area for potential infection of the tumor by the virus. Rather than intact virus, viral or other plasmids or expression vectors incorporating nucleic acid for generation of the virus may be injected into the tumor for uptake by tumor cells and generation of intact virus within the cells for effecting the treatment. Suitable expression vectors include plasmids capable of expression of a DNA (eg genomic DNA or cDNA) insert encoding viral proteins necessary for generation of the virus. An expression vector will typically include transcriptional regulatory control sequences to which the inserted nucleic acid is operably linked. By "operably linked" is meant the nucleic acid insert is linked to the transcriptional regulatory control sequences for permitting transcription of the inserted sequence(s) without a shift in the reading frame of the insert. Such transcriptional regulatory control sequences include promotions for facilitating binding of RNA polymerase to initiate transcription, and expression control elements for enabling binding of ribosomes to transcribed mRNA.

More particularly, the term "regulatory control sequence" as used herein is to be taken to encompass any DNA that is involved in driving transcription and controlling (ie regulating) the level of transcription of a given DNA sequence. For example, a 5' regulatory control sequence is a DNA sequence located upstream of a coding sequence and which may comprise the promotor and the 5' untranslated leader sequence. A 3' regulatory control sequence is, a DNA sequence located downstream of the coding sequence(s), which may comprise suitable transcription terminated (and/or) regulation signals, including one or more polyadenylation signals. As used herein, the term "promotor" encompasses any DNA sequence which is recognised and bound (directly or indirectly) by a DNA-dependant ENA polymerase during initiation of transcription. A promotor includes the transcription initiation site, and binding sites for transcription initiation factors and RNA polymerase, and can comprise various other sites or sequences (eg enhances), to which gene expression regulatory proteins may bind.

Numerous expression vectors suitable for transfection of mammalian cells are known in the art. Expression vectors suitable for transfection of mammaliam cells include pSV2neo, pEF-PGk.puro, pTk2 and non-replicating adenoviral shuttle vectors incorporating the polyadenlation site and elongation factor 1-x promotor and pAdEasy based expression vectors most preferably incorporating a cytomegaloviros (CMV) promotor (eg see He et al, 1998). The plasmid pEF-BOS which employs the polypeptide elongation factor—alpha 2 as the promotor may also be utilised.

cDNA encoding the viral proteins necessary for generation of the virus may be prepared by reverse transcribing the viral RNA genome or fragments thereof and incorporated into a suitable vector utilising recombinant techniques well known in the act as described in for example Sambrook et al (1989), Molecular Cloning: A Laboratory Manual, Second Ed., Cold Spring Harbour Laboratory Press, New York, and Ausubel et al., (1994), Current Protocols in Molecular Biology, USA, Vol. 1 and 2.

Rather than cDNA, cells may be transfected with viral RNA extracted from purified virions or for instance RNA transcripts may be generated in vitro from xDNA templates utilising bacteriophage T7 RNA polymerase as described in Ansardi, D. C., et al, 2001. Similarly, a single plasmid or RNA molecule may be administered for expression of viral proteins and generation of virus, or a plurality of plasmids or RNA molecules encoding different ones of the viral proteins may be administered for transfecting the cells and generation of the virus.

Plasmids or RNA may be administered directly to tumors either topically or by injection for uptake by the tumor cells in the absence of a carrier vehicle for faciliating transfection of the cells or in combination with such a vehicle. Suitable carrier vehicles include liposomes typically provided as an oil-in-water emulsion conventionally known in the art. Liposomes will typically comprise a combination of lipids, particularly phospholipids such as high phase transition temperature phospholipids usually with one or more steroids or steroid precursors such as cholesterol for providing membrane stability to the liposomes. Examples of lipids useful for providing liposomes include phosphatidyl compounds such as phosphatidylglycerol, phosphatidylcholine, phosphatidylserine, sphingolipids, phosphatidylethanolamine, cerebrosides and gangliosides. Diacyl phosphatidylglycerols are particularly suitable, where the lipid moiety contains from 14 to 18 carbon atoms and more preferably from 16 to 18 carbon atoms, and is saturated.

Interaction of the liposomes with the target cells may be passive or active. Active targeting involves modification of the liposome by incorporating in the liposome membrane a specific ligand whir binds or otherwise interacts with the corresponding ligand expressed by the target cells. Such ligands include for example a monoclonal antibody or binding fragment thereof (eg. an Fab or F(ab')$_2$) fragment a sugar or glycolipid moety, or a viral protein viral proteins or monoclonal antibodies specific for $\alpha_2\beta_1$, are particularly preferred.

Normally, tissue surrounding the tumor will also be injected or otherwise treated with the virus given the possibility of malignant cells being present in the tissue. If the tumor is not detected until it is relativity advanced, surrounding tissue may be injected with the virus following surgical excision of the tumor itself.

Rather than being injected directly into a malignant tumor, the inoculant may be administered systemically by intravenous injection into the blood stream of the recipient at a location adjacent to the tumor site for delivery to the tumor. Similarly, the inoculant may be administered subcutaneously, intraperitoneally or for instance, intramuscularly if deemed appropriate. Generally, however, when intact virus is administered, direct injection into the tumor is preferred given the possibility of the existence of antibodies specific for the virus and thereby the potential decreased efficacy of alternate modes of virus delivery.

The inoculant may also be applied topically to tumors either alone or in combination with direct injection of the inoculant into the tumor. Topical treatment of the tumor may be achieved by dropwise application of a pharmaceutical composition comprising the inoculant and a suitable pharmaceutically acceptable carrier for maintaining the integrity of the inoculant for infection of the malignant cells or by swabbing the tumor with an applicator impregnated with such a composition. The applicator may comprise a wad or pad of suitable material that has been dipped in the composition. In the case of treatment of melanoma on the skin, the inoculant may be applied by way of an applicator impregnated with the inoculant and which is adapted for being held against the malignant site to be treated such that the inoculant is in contact with the skin. In this instance, the applicator may comprise a patch, wad or the like impregnated with the inoculant and which is further provided with an adhesive surface or surfaces such as in the case of a sticking plaster, for adhering to the skin surrounding the melanoma and thereby hold the inoculant in contact with the melanoma. Typically, intact virus will be administered to the mammal to effect treatment.

Generally, one or more small incisions will be made into the malignancy and/or surrounding tissue to provide a site of entry for the virus into same.

In the case of ovarian cancer, or cancer in the vicinity of an ovary, the echovirus may be delivered directly to the ovary or affected site using a catheter or other suitable application instrument via insertion of the catheter or selected instrument along the corresponding fallopian tube.

The pharmaceutically acceptable carrier used for inoculating the recipient with virus and/or nucleic acid or plasmids comprising viral nucleic acid for generation of the virus within the target cells may be a fluid such as physiological saline, or any other conventionally known physiologically acceptable medium deemed appropriate such as commercially available gels suitable for pharmaceutical use and for administering the inoculant to the site of treatment. The carrier will typically be buffered to physiological pH and may contain suitable preservatives and/or antibiotics.

The inoculant will generally contain from about $1\times10^2$ to about $1\times10^{10}$ plaque forming units per ml of the inoculant. Preferably, the inoculant will contain greater than about $1\times10^5$ plaque forming units per ml of inoculant. The amount of inoculant administered to the patient may be readily determined by the attending physician or surgeon in accordance with accepted medical practice taking into account the general condition of the patient, the stage and location of the malignancy together with the overall size and distribution of the area to be treated with the virus. Typically, the patient will be treated with an initial dose of the virus and subsequently monitored for a suitable period of time before a decision is made to administer further virus to the patient pending factors such as the response of the patient to the initial administration of the v and the degree of viral infection and malignant cell death resulting from the initial treatment Desirably, an individual will be treated with the virus over a period of time at predetermined intervals. The intervals may be daily or range from 24 hours up to 72 hours or more as determined appropriate in each circumstance. A different virus may be administered each time to avoid or minimise the effect of any immune response to a previously administered virus, and a course of treatment may extend for one to two weeks or more as may be determined by the attending physician. Most preferably, virus to which the mammal has not previously been exposed or to which the mammal generates a relatively minor immune response as maybe determined by standard techniques will be administered.

While readily available known echoviruses may be suitably employed in a method of the invention, a virus modified or engineered using conventional techniques may also be utilised. For instance, a virus may be modified to employ additional cell adhesion molecules as cell receptors. As an example, a virus maybe modified using site-directed mutagenesis so that the peptide motif "RGD" is expressed on the viral capsid surface. The RGD motif is recognised by $\alpha_v$ integrin heterodimers and this capsid modification may for instance allow the virus to bind the integrin $\alpha_2\beta_1$, a cell adhesion molecule which has been shown to be upregulated on melanoma lesions (Natalia P. G; 1997) as has $\alpha_2\beta_1$, potentially leading to enhanced uptake of the virus by the target cell.

In order that the nature of the present invention may be more dearly understood, preferred forms thereof will now be described with reference to the following non-limiting examples.

EXAMPLE 1

Materials and Methods 1.1. Cell Lines

IGROV-1, A2780, DU145, PC3, AsPC-1, PANC-1, T47-D, MDA-MB361, MDA-MB453, MDA-MB231, and MCF-7 cancer cell lines were obtained from the Garvan Institute, Sydney, New South Wales, Australia. BT-20, MDA-MB157, SK-BR-3, ZR-75-1, HCT116, LIM2537, SW480, SW620, 2008, JAM, OVCA-429, OVCAR-3, OVHS-1, OWA-42, SKOV-3, and DOV13 cancer cell lines were obtained from Peter MacCullum Cancer Institute, Melbourne, Victoria, Australia. SkMel28 Cells were obtained from Dr Ralph, Department of Biochemistry and Molecular Biology, Monash University, Victoria, Australia. HeLa cells were obtained from Margery Kennett, Entero-respiratory Laboratory, Fairfield Hospital Melbourne, Victoria, Australia. All cells were cultured under standard conditions (37° C. in a 5% $CO_2$ atmosphere) in RPMI containing 2-5% Fetal Calf Serum (FCS) and antibiotics excluding BT-20 cells which were cultured in α-CMEM media, and SkMel28 and HeLa cells which were cultured in DMEM media. All cells used were routinely checked for presence of mycoplasma by ELISA (Roche Molecular Systems, CA, USA).

1.2. Viruses

Coxsackievirus A21 (CAV21) prototype strain, Kuykendall; Coxsackievirus B3 (CVB3) prototype strain, Nancy; Echovirus (EV1) prototype strain, Farouk; Echovirus (EV7) prototype strain, Wallace; and Poliovirus 1 (PV1) prototype strain, Mahoney; were obtained from Dr Margery Kennett, Enterorespiratory Laboratory, Fairfield Hospital, Melbourne, Victoria, Australia. All viruses were propagated and titrated in HeLa cells.

1.3 Monoclonal Antibodies (MAbs)

The anti-DAF MAb VIIIA7, which recognizes the third SCR of DAF, was obtained from Dr T. Kinoshita, Osaka University, Osaka, Japan and the anti-DAF mAb IH4 was a gift from Dr Bruce Loveland, Austin Research Institute, Heidelberg, Victoria, Australia. The anti-CAR MAb RmcB was obtained from Dr. J. M. Bergelson, Dana Farber Cancer Institute, Boston, Mass. The anti-β2-microglobulin MAb 918 was obtained from Dr. P. Minor, NIBSC, Hertfordshire, England. The anti-$\alpha_2\beta_1$ MAb AK7, recognizing the $\alpha_2$ subunit, and the control antibody anti-GPIV (platelet membrane glycoprotein) MAb PTA-1 were obtained from Professor Gordon Burns, Department of Medical Biochemistry and Cancer Research, University of Newcastle, NSW, Australia. The anti-ICAM-1 MAb IH4 was obtained from Dr Andrew Boyd from the Queensland Institute for Medical Research, Queensland, Australia.

1.4. Flow Cytometric Analysis

Enteroviral receptor surface expression on cancer cells was analysed by flow cytometry. Dispersed cells ($1\times10^6$) were incubated for 20 minutes on ice with the appropriate MAb (5 μg/ml diluted in PBS) for 20 minutes. Cells were washed with PBS and pelleted by centrifugation before resuspension in 100 μl of 1:50 dilution of R-phycoerythrin-conjugated $F(ab')_2$ fragment of goat anti-mouse immunoglobulin (Dako, A/S, Denmark). Cells were again incubated on ice for 20 minutes, washed, pelleted and resuspended in PBS prior to flow cytometric analysis. Cell surface receptor expression was analysed using a FACStar™ Analyser (Becton Dickenson, Sydney, Australia).

1.5. Virus Infectivity Assay

Confluent monolayers of cancer cell lines were inoculated with 10-fold serial dilutions (100 μl/well in triplicate or quadruplicate) of CAV21, CVB3, EV1, EV7 or PV1 in DMEM containing 1% fetal calf serum (FCS) and incubated at 37° C. in a 5% $CO_2$ environment for 72 hours. To determine cell survival, plates were incubated with 100 μl/well of crystal violet methanol solution (0.1% crystal violet, 20% methanol, 20% formaldehyde, phosphate buffered saline (PBS)) for 24 hours and washed in distilled water.

The endpoint of a limiting dilution assay is the dilution of virus that affects 50% of test units. Statistical procedures were employed to calculate the endpoint using the Reed and Muench method (Reference). Endpoints were expressed as the 50% tissue culture infectious dose per milliliter ($TCID_{50}$/ml).

Where cell monolayer pretreatment with anti-receptor monoclonal antibodies was required, cells were incubated with 100 μl of anti-$\alpha_2\beta_1$ AK7MAb (20 μg/ml diluted in PBS) for 1 hour at 37° C. Cell monolayers were then inoculated in duplicate samples of appropriate viral dilution and incubated at 37° C. in 5% $CO_2$ environment for 72 hours before staining as described above.

Photomicrographs were taken at 24, 48 or 72 hours at 100×magnification (Olympus IX-FLA) using an inverted microscope.

1.6. Virus Purification

Six-well tissue culture plates containing confluent monolayers of DOV13 cells were inoculated with 500 μl EV1 (multiplicty of infection [moi]=$10^5$ $TCID_{50}$/ml) for 1 hour at 37° C. Unbound virus was removed by washing three times with methionine/cysteine free DMEM (ICN Biomedical, Ohio, USA) and cell monolayers were incubated in 1.3 ml of this media for a further 2 hours at 37° C. before addition of 300 μCi of [$^{35}$S]-methionine translabel (ICN Biomedical, Ohio, USA). Infected monolayers were incubated overnight at 37° C. in a 5% $CO_2$ environment Following three freeze/thaw cycles viral lysates were purified in a 5-30% sucrose gradient by velocity centrifugation for 95 minutes at 36,000 rpm in a Beckman XL-90 ultracentrifuge (SW41ti Rotor). Fractions were collected from the bottom of each tube and monitored by liquid scintillation counting (Wallac 1450' MICROBETA® TRILUX, Finland) to locate 160S viral peak fraction used in viral binding assays.

Non-radiolabelled EV1 virions were purified in parallel gradients with peak infectious fractions pooled and dialysed against phosphate buffered saline (PBS). Ultraviolet (UV)

light-inactivated EV1 was produced by exposing 1.0 ml of purified EV1 in PBS/well ($5\times10^5$ $TCID_{50}$) in a 6-well plate to a 15 watt UV light for 30 seconds. Viral inactivation was assessed by microtiter plate lytic infectivity cell assays.

Figure 2:
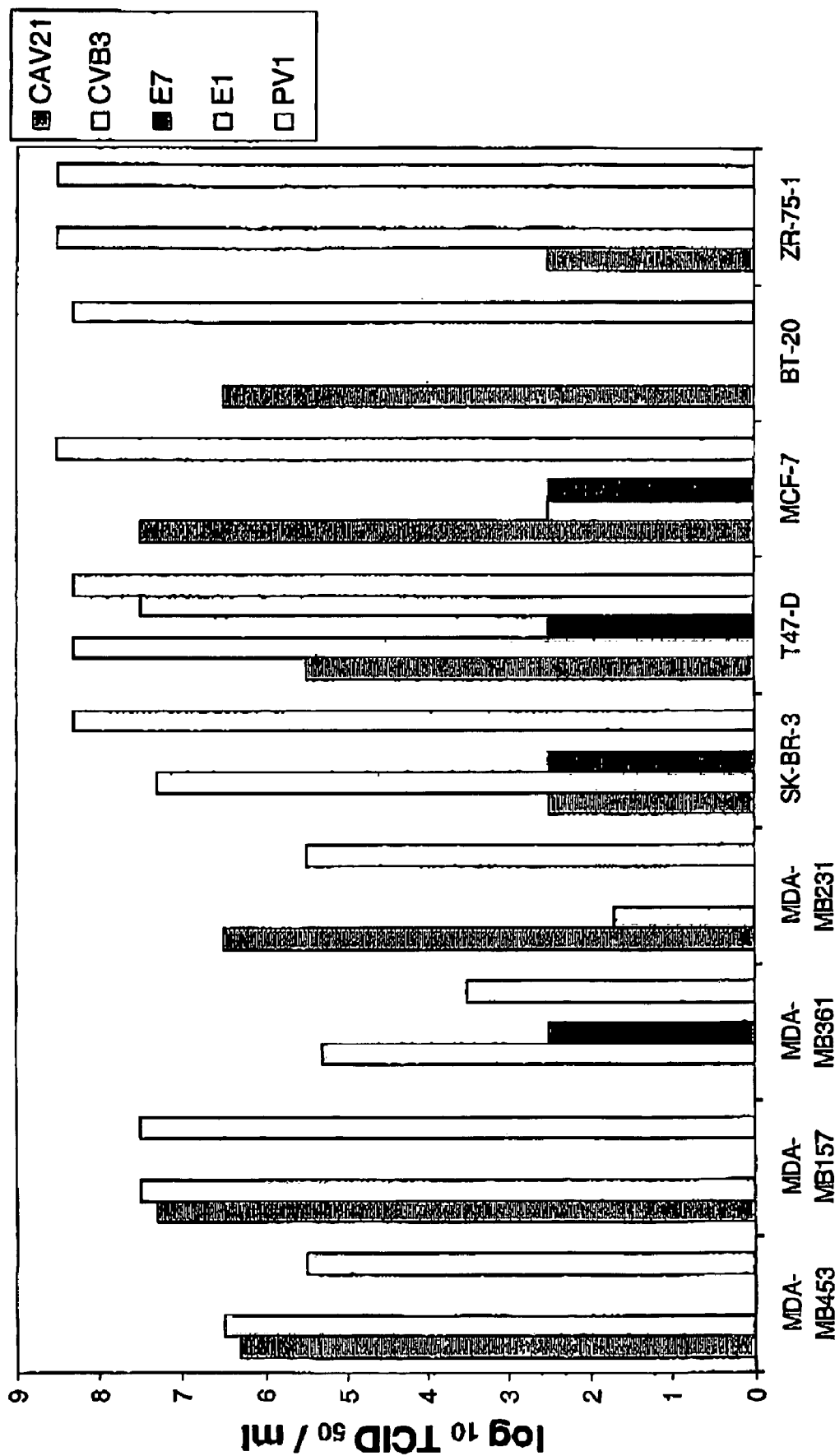
FIG. 2 shows lytic infection of breast cancer cells by the enteroviruses CAV21, CVB3, EV1, EV7 and PV1. Fifty percent endpoint titres were calculated and oncolysis was considered significant if the TCID$_{50}$/ml endpoint was $10^4$ or greater.

1.7. Radiolabeled Virus Binding Assay

Approximately $1\times10^6$ cells resuspended in 800 μl of RPMI containing 1% bovine serum albumin (BSA) were incubated in the presence of 20 μg/ml of MAb (anti-$\alpha_2\beta_1$ or anti-DAF diluted in PBS) for 1 hour at 4° C. followed by the addition of 300 μl ($1\times10^6$) of [$^{35}$S]-methionine labeled 160S EV1. After incubation at 4° C. for 2 hours cells were washed four times with serum free media and cell pellets dissolved in 200 μl 0.2M NaOH-1% SDS before the level of [$^{35}$S]-methionine labeled virus bound was determined by liquid scintillation counting from triplicate samples. (Wallac 1450 MICRO-BETA® TRILUX, Finland). Results were expressed as means±SE.

1.10. Sodium Dodecyl Sulfate—Polyacrylamide Gel Electrophoresis (SDS-PAGE)

[$^{35}$S]-methionine labeled viral fractions were analysed by polyacrylamide gel electrophoresis (PAGE) and visualised by autoradiography. [$^{35}$S]-methionine labeled 160S EV1 fractions were incubated with sample reducing buffer (250 mM TRIS, 0.2 g w/v SDS, 20% v/v glycerol, 10% v/v 2-mercaptoethanol and 0.01% w/v bromophenol blue, pH 6.8) for 10 minutes at 95° C. denaturing the virion. Denatured 160S vial peak fractions were then separated on a 15% Tris-HCl precast gel (Bio-Rad READY GEL®, CA, USA) in conjunction with a Benchmark prestained midrange protein ladder (GIBCO, USA) at 180 V for 45 minutes. Visualisation of the major structural proteins and analysis of viral purity was by autoradiography on Hyperfilm MP (Amersham International, England) after 96 hour exposure.

1.11 Cell Cytotoxicity Assay

Cell suspensions of human peripheral blood lymphocytes, OVHS-1 and DOV-13 cells were challenged with EV1 (moi=1.0 $TCID_{50}$/cell) and incubated for 24 h at 37° C. Levels of cell cytolysis were calculated as a function of release of LDH (a stable cytosolic enzyme that is released upon cell lysis), assessed by using a CYTOTOX 96® kit (Promega Corp. Maddison, Wis. USA) as per the manufactures instructions.

1.12 Culture of Spheroids and Spheroid Infectivity Assay

DOV-13 cells were seeded in a 24-well plate at 500 or 5000 cells per well in 1 ml of RPMI 1640 containing 5% FCS onto a semi-solid 0.5% agarose layer. Cells were incubated for 48 h at 37° C. in a 5% $CO_2$ atmosphere to allow spheroids to form, before the addition of EV1 ($10^5$ $TCID_{50}$).

1.13 Intraperitoneal Tumour Xenograft Model in SCID Mice

Six to eight week old male BALB/c SCID mice were housed in pathogen-free conditions according to a protocol approved by the university of Newcastle Animal Care and Ethics Committee. OVHS-1 cells were harvested with 0.05% tryps resuspended in RPMI containing 10% FCS and pelleted by centrifugation Cells were washed and resuspended in PBS before mice were injected intraperitoneally (i.p.) with $1\times10^6$ cells in 200 μl. Fourteen days later, the mice were divided into three groups (n=5) and treated i.p. with phosphate buffered saline (PBS), or $10^5$ $TCID_{50}$ of either UV-inactivated EV1 or infectious EV1. The animals were weighed on a weekly basis and were sacrificed when tumours exceeded 20% of their body weight The weights of the treated mice were compared to healthy BALB/c SCID mice bearing no tumours.

1.14 Determination of Viremia by Real-Time PCR

Sera from infected mice were analyzed for viremia using real-time quantitative RT-PCR. Briefly, viral RNA was extracted from 10 μl of serum using a QIAamp® Viral RNA mini kit (Qiagen, Clifton Hill, Victoria, Australia) and eluted in a final volume of 40 μl according to manufacturer's instructions. Primers and probe for determination of EV1 viral RNA levels were designed using the PRIMER EXPRESS™ 1.5 software (Applied Biosystems, Foster City, Calif., USA) and were based on the previously published EV1 sequence (Genbank accession number AF029859); forward primer (5'-CAAGACAGGGACCAAAGAGGAT-3') (SEQ ID NO: 1), reverse primer (5'-CCACTCGCCTGGTTGTAATCA-3') (SEQ ID NO: 2') and 6-FAM-labeled MGB-probe (5'-CCAATAGCTTCAACAATT-3') (SEQ ID NO: 3). One-step RT-PCR was performed using PLATINUM® Quantitative RT-PCR THERMOSCRIPT™ One-Step System on an ABI 7000 sequence detector. For generation of the standard curve, 10-fold dilutions of EV1 viral stock ($1\times10^6$ $TCID_{50}$/ml) was amplified with optimized concentration of primers and probe. In a volume of 25 μl, the reaction mixture comprised; 1×THERMOSCRIPT™ reaction mix, 500 nM forward, 900 nM reverse primer, 250 nM probe, 500 nM ROX, 0.5 μl THERMOSCRIPT™ Plus/Platinum Taq Mix and 5 μl extracted RNA. Thermal cycling conditions were subjected to 30 min at 60° C., followed by 5 min at 95° C. and then 40 cycles of 15 s at 95° C. and 1 min at 60° C.

EXAMPLE 2

Viral Mediated Oncolysis of Cancer Cell Lines 2.1 Expression of Enterovirus Receptors on the Surface of Breast Cancer Cells To determine the relative expression levels of selected enteroviral cell surface receptors used by enteroviruses flow cytometric analysis was performed. The selected group of receptors consisted of ICAM-1 employed by CAV21; DAF employed by EV7, CAV21, CVB3; CAR used by CVB3; and integrin $\alpha_2\beta_1$ used by EV1. Due to the unavailability of Mab against the PVR receptor, no expression levels of PVR were determined.

Nine breast cancer cell lines were analysed including BT-29, MCF-7, MDA-MB157, MDA-MB231, MDA-MB361, MDA-M453, SK-BR-3, T47-D and ZR-75-1. The cell lines were incubated with either anti-ICAM-1 (IH4), anti-CAR (RmcB), anti-DAF (VIIIA7) or anti-$\alpha_2\beta_1$ (AK7).

ICAM-1 expression was significant in six of the nine lines while DAF appeared to be expressed at relatively low levels in all the cell lines. Moderate levels of CAR expression were evident on seven of the nine lines, while minimal levels of $\alpha_2\beta_1$ expression were present on the surface of eight of the breast cancer lines (FIG. 1).

2.2. Oncolysis of Breast Cancer Cells by Selected Enteroviruses

Lytic infectivity assays were performed on all nine of the breast cancer cell lines to determine their susceptibility to a select group of enteroviruses, CAV21, CVB3, EV1, EV7 and PV1 (FIG. 2). A cell line was considered to be highly susceptible to oncolysis if the tissue culture infectious dose at a fifty percent endpoint per milliliter ($TCID_{50}$/ml) was calculated to be $10^4$ or greater. CAV21 and CVB3 induced significant lysis in six of the nine breast cancer cell lines. In general breast cancer cells were not susceptible to lytic infection by the echoviruses EV1 and EV7 excluding one cell line T47-D which demonstrated considerable susceptibility to EV1. PV1 caused substantial oncolysis in eight of the nine breast cancer cell lines (FIG. 2).

Figure 3:
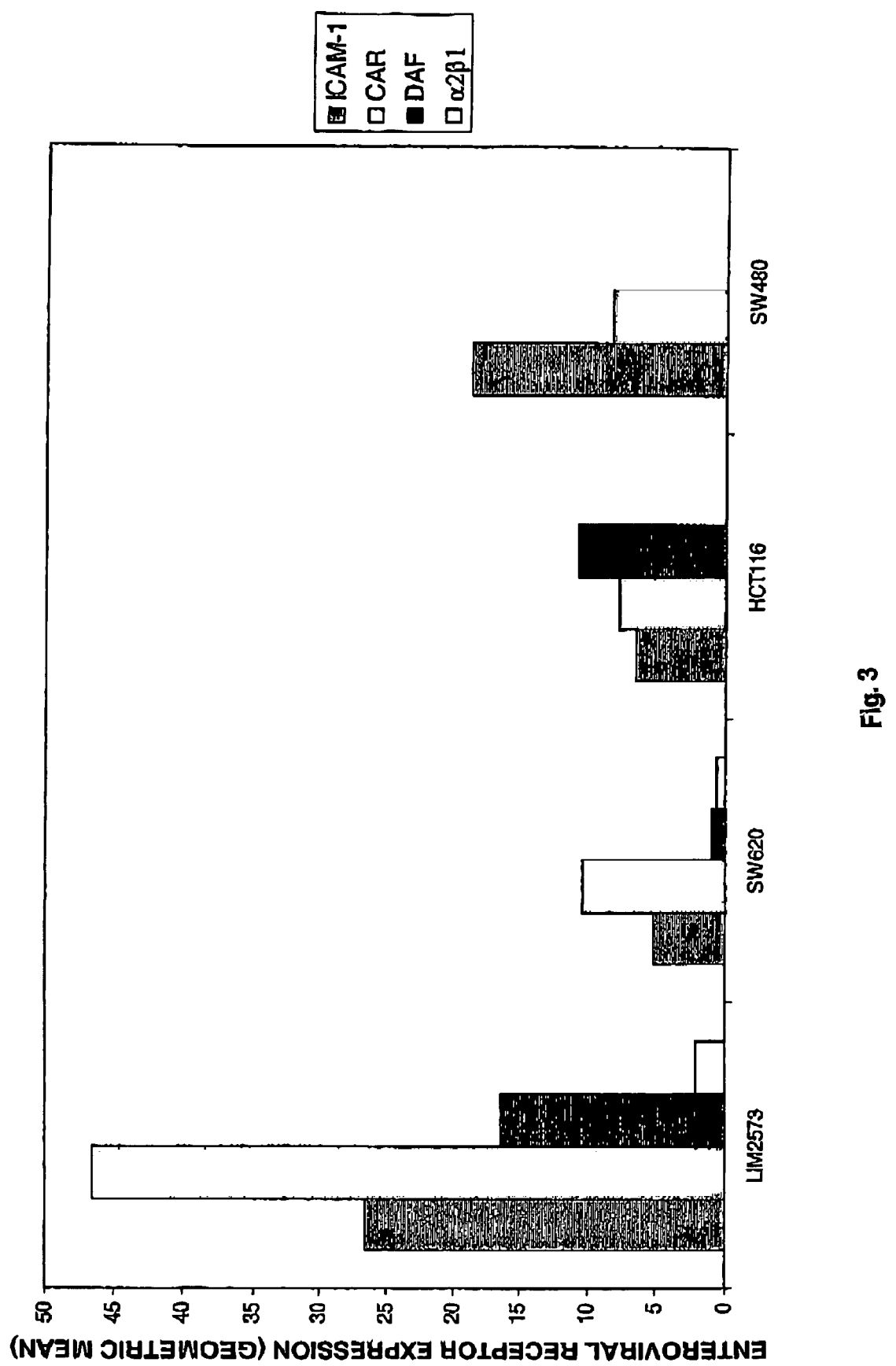
FIG. 3 shows flow cytometric analysis of the levels of surface expressed ICAM-1, CAR, DAF and $\alpha_2\beta_1$ on the surface of colorectal cancer cells. The colorectal cancer cells were incubated with R-phycoerythrin-conjugated F(ab')$_2$ fragment of goat anti-mouse immunoglobulin in the presence or absence of corresponding monoclonal antibodies specific for these receptors. The geometric mean of the conjugate sample was subtracted from the geometric mean of the enteroviral receptor sample revealing the relative level of expression of the receptor.

2.3. Expression of Enterovirus Receptor on the Surface of Colorectal Cancer Cells Four colorectal cancer cell lines (HCT116, LIM2537, SW480 and SW620) were analysed for expression of ICAM-1, CAR, $\alpha_2\beta_1$ and DAF by flow cytometry. Significant levels of ICAM-1 and DAF expression were observed on two of the cell lines. Moderate levels of CAR appeared to be expressed on all four lines, while significant levels of $\alpha_2\beta_1$ expression were not observed (FIG. 3).

2.4. Oncolysis of Colorectal Cancer Cells by Selected Enteroviruses

Figure 4:
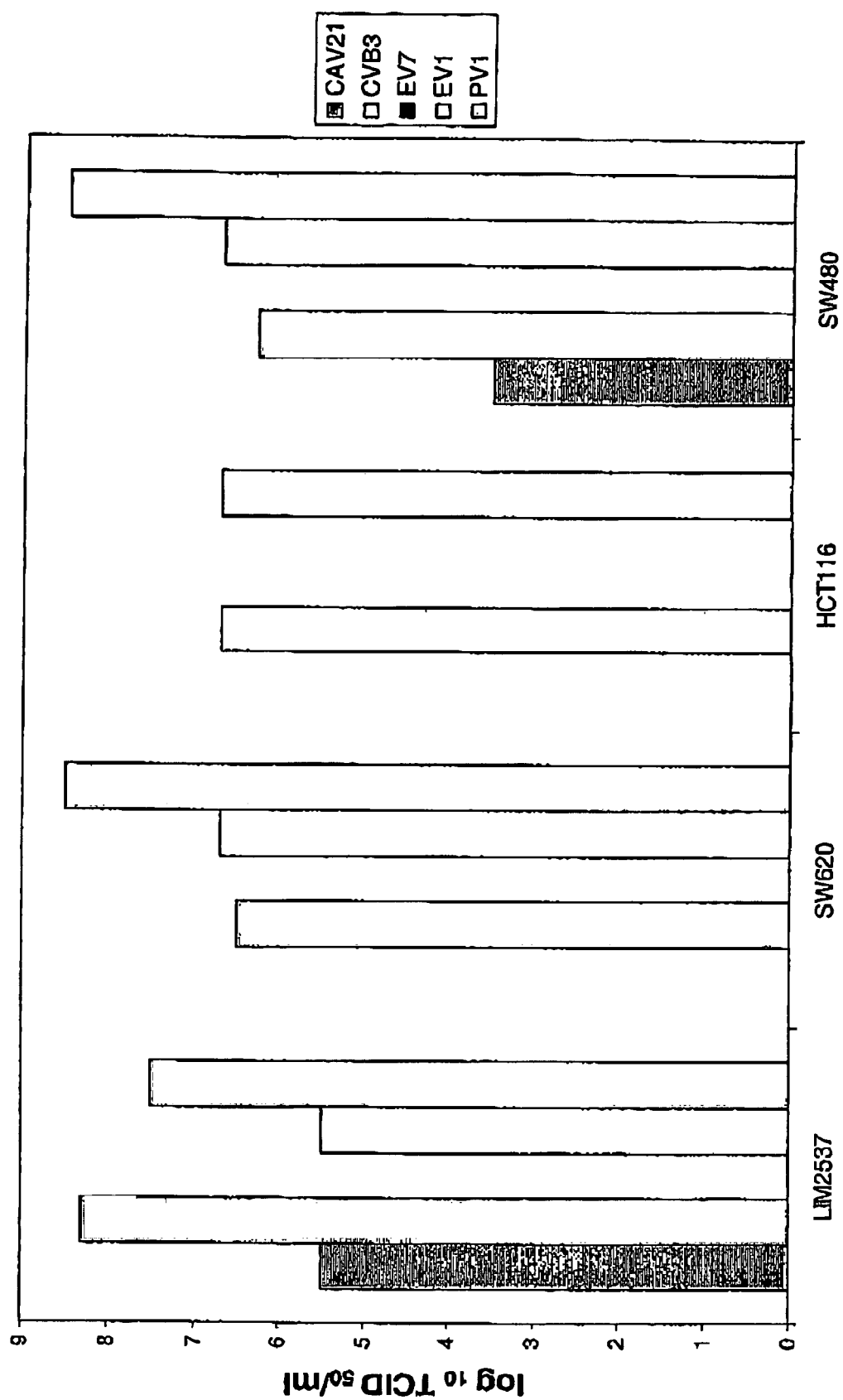
FIG. 4 shows lytic infection of colorectal cancer cells by the enteroviruses CAV21, CVB3, EV1, EV7 and PV1. Fifty percent endpoint titres were calculated and oncolysis was considered significant if the TCID$_{50}$/ml endpoint was $10^4$ or greater.

CAV21, CVB3, EV1, EV7 and PV1 were titrated in all four colorectal cancer cell lines. Significant levels of oncolysis by CVB3 and PV1 were observed in all of the cell lines (FIG. 4). However, significant cell lysis induced by CAV21 occurred in only one of the four cell lines (LIM2573). This cell line exhibited the highest level of ICAM-1 expression. Despite very low expression levels of $\alpha_2\beta_1$, EV1 lytically infected three of the cell lines while al cells were refractile to EV7 infection.

Figure 5:
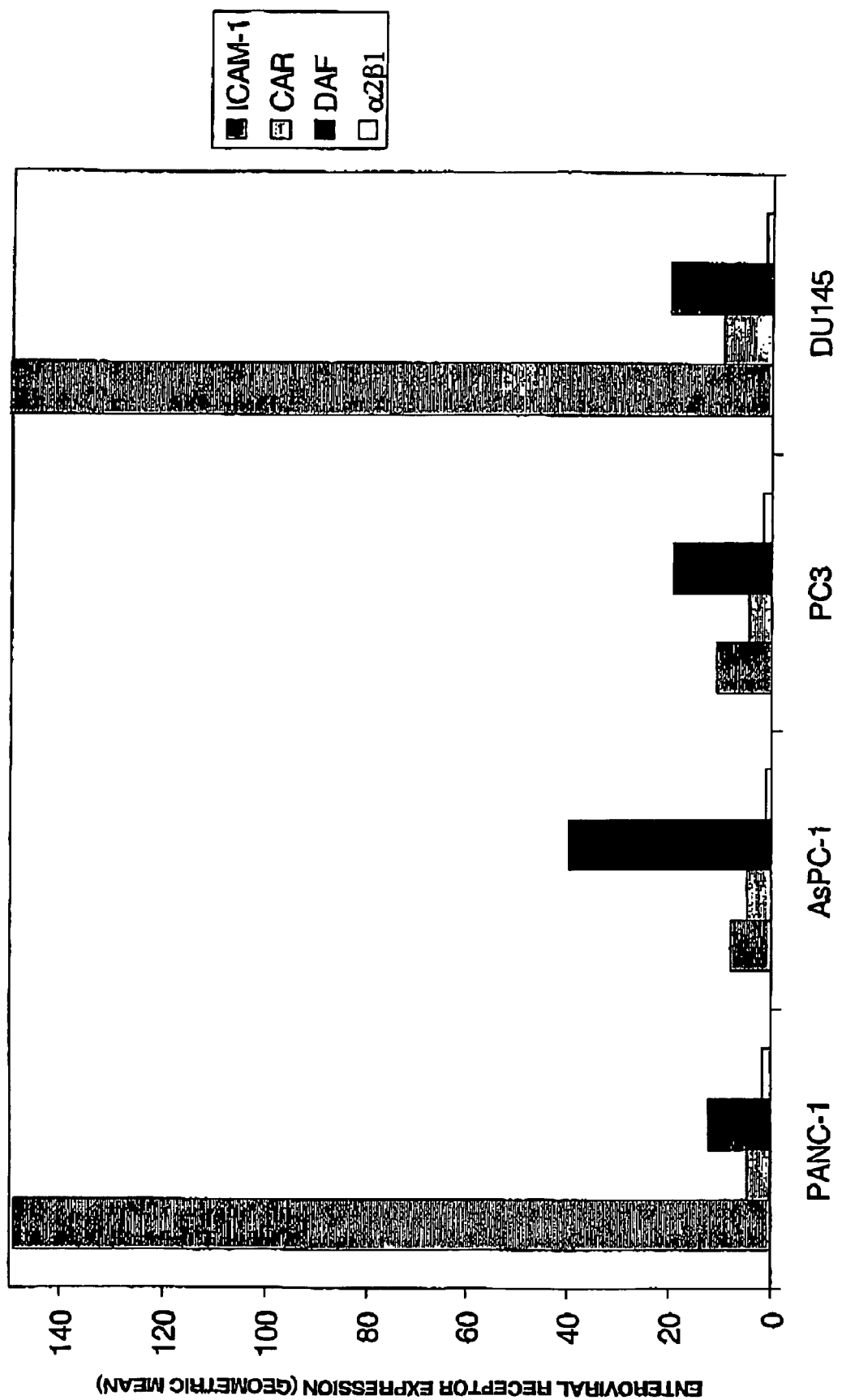
FIG. 5 shows flow cytometric analysis of the levels of surface expressed ICAM-1, CAR DAF and $\alpha_2\beta_1$ on the surface of the prostate or pancreatic cancer cells. The prostate or pancreatic cancer cells were incubated with R-phycoerythrin-conjugated F(ab')$_2$ fragment of goat anti-mouse immunoglobulin in the presence or absence of corresponding monoclonal antibodies specific for these receptors. The geometric mean of the conjugate sample was subtracted from the geometric mean of the enteroviral receptor sample revealing the relative level of expression of the receptor.

2.5. Expression of Enter Receptors on the Surface of Prostate and Pancreatic Cancer Cells Prostatic cancer cell lines including DU145 and PC3, and pancreatic cancer cell lines including AsPC-1 and PANC-1, were analysed for expression of ICAM-1, DAF, CAR and $\alpha_2\beta_1$. Significant levels of ICAM-1 was expressed on both of the prostatic cell lines and on one of the pancreatic lines. Moderate CAR and DAF expression was found on all four of the cell lines while $\alpha_2\beta_1$ expression appeared to be minimal (FIG. 5).

2.6 Oncolysis of Prostate and Pancreatic Cancer Cells

Figure 6:
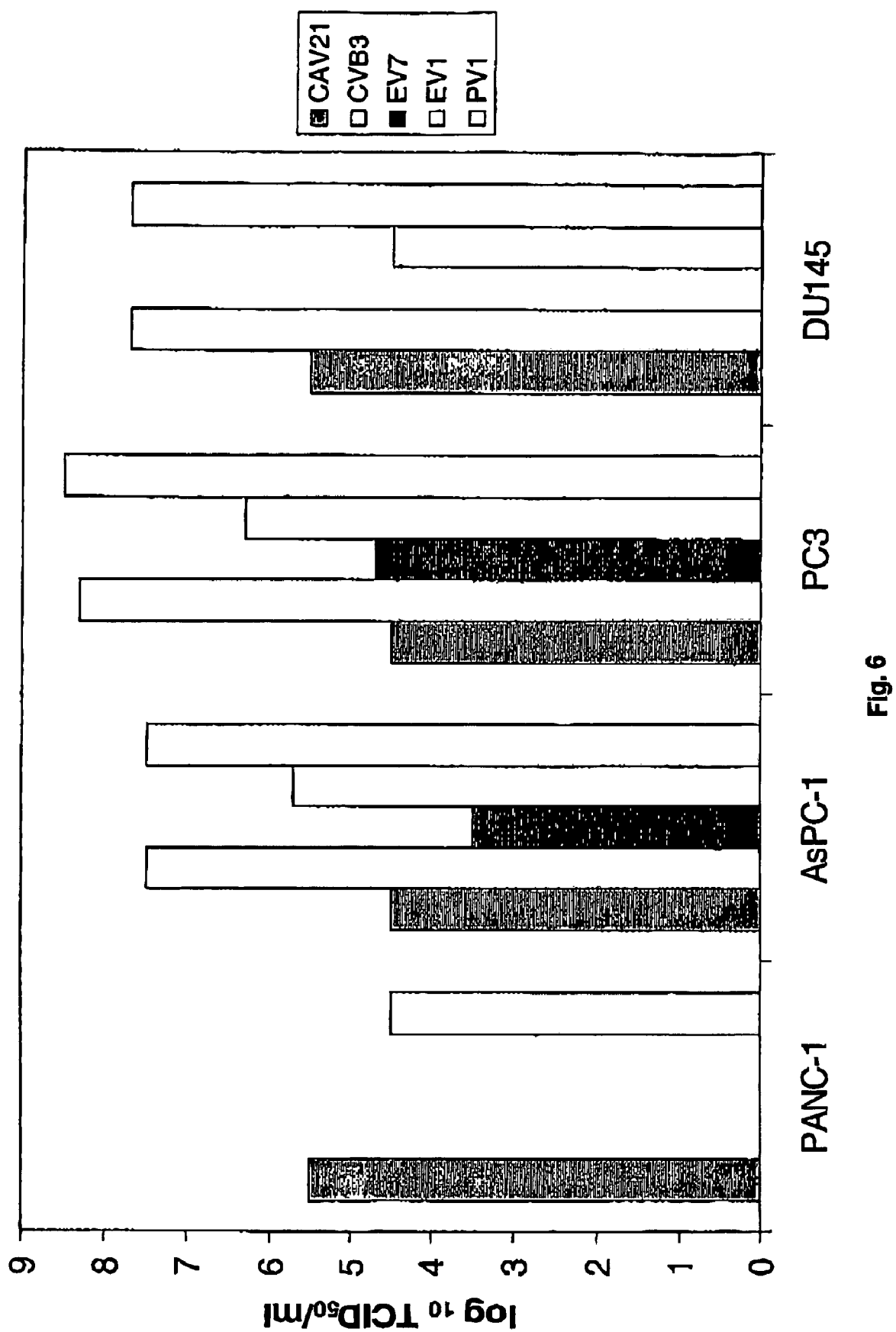
FIG. 6 shows lytic infection of prostate and pancreatic cancer cells by the enteroviruses CAV21, CVB3, EV1, EV7 and PV1. Fifty percent endpoint titres were calculated and oncolysis was considered significant if TCID$_{50}$/ml endpoint was $10^4$ or greater.

The susceptibility of two prostate cancer cell lines and two pancreatic cancer cell lines to enteroviruses CAV21, CVB3, EV1, EV7 and PV1 was examined in microtitre plate lytic infections. The prostatic cancer cell lines were susceptible to all the viruses excluding EV7 in the case of DU145. PANC-1 was only infected by CAV21 and PV1, whereas the other pancreatic cancer cell line AsPC-1 exhibited oncolysis by all viruses excluding EV7 (FIG. 6).

2.7 Expression of Enterovirus Receptors on the Surface of Ovarian Cancer Cells

Figure 7:
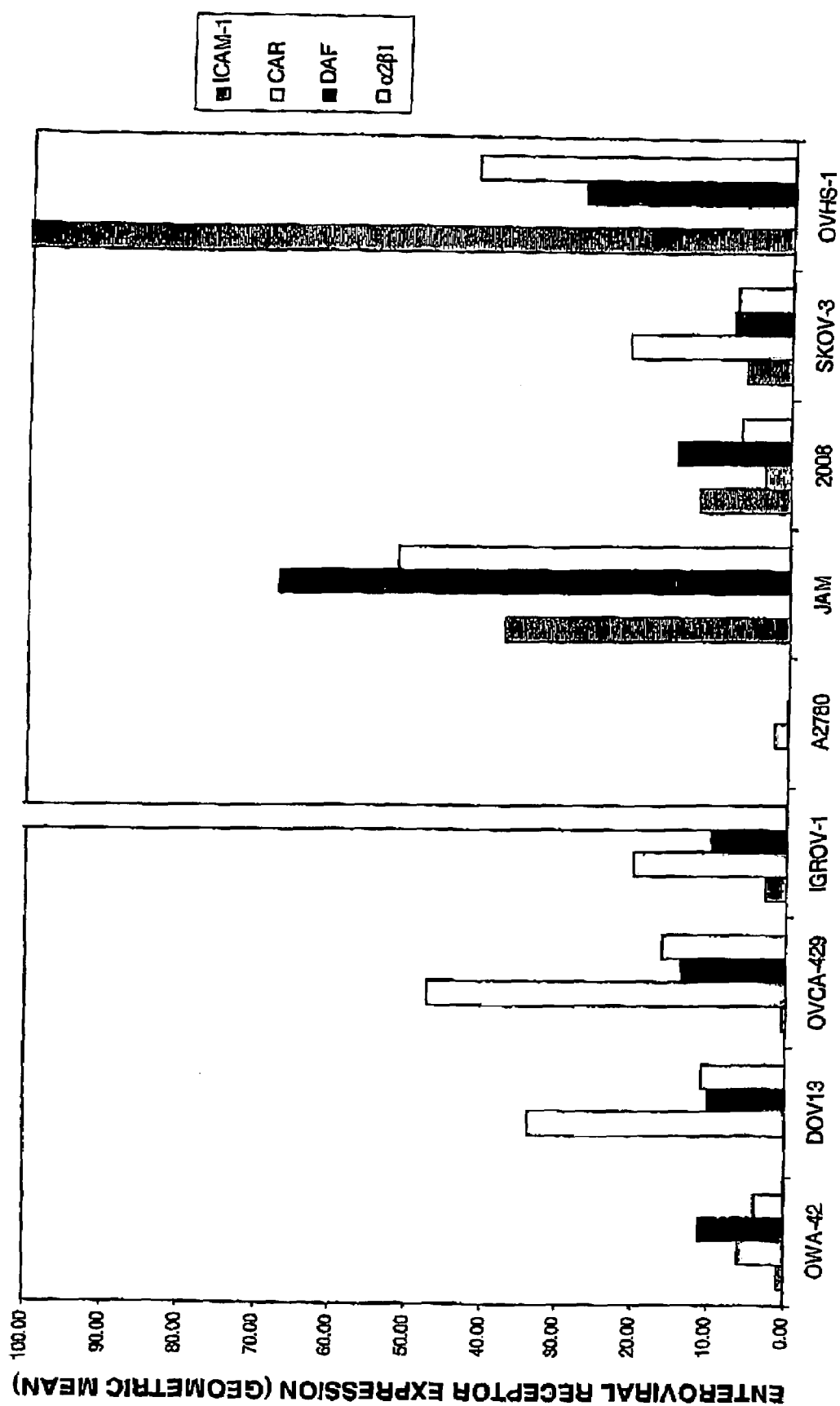
FIG. 7 shows flow cytometric analysis of the levels of surface expressed ICAM-1, CAR, DAF and $\alpha_2\beta_1$ on the surface of ovarian cancer cells. The ovarian cancer cells were incubated with R-phycoerythrin-conjugated F(ab')$_2$ fragment of goat anti-mouse immunoglobulin in the presence or absence of corresponding monoclonal antibodies specific for these receptors. The geometric mean of the conjugate sample was subtracted from the geometric mean of the enteroviral receptor sample revealing the relative level of expression of the receptor.

Ovarian cancer cell lines were examined for expression of enterovirus receptors ICAM-1, CAR, DAF and $\alpha_2\beta_1$. Nine cell lines were included in this study: A2780, DOV13, IGROV-1, JAM, OVCA-429, OVHS-1, OWA-42 SKOV-3 and 2008. Significant levels of ICAM-1 were expressed on two of the nine cell lines while moderate levels of CAR expression were present on six of the nine. DAF was expressed at high to moderate levels on all but one of the ovarian cancer cell lines. Eight of the nine ovarian cancer cell lines exhibited moderate to high level expression of $\alpha_2\beta_1$ (FIG. 7), with an additional ovarian cancer cell line (OVCAR-3) expressing significant levels of $\alpha_2\beta_1$ (data not shown).

2.8 Oncolysis of Ovarian Cancer Cell Lines

Figure 8:
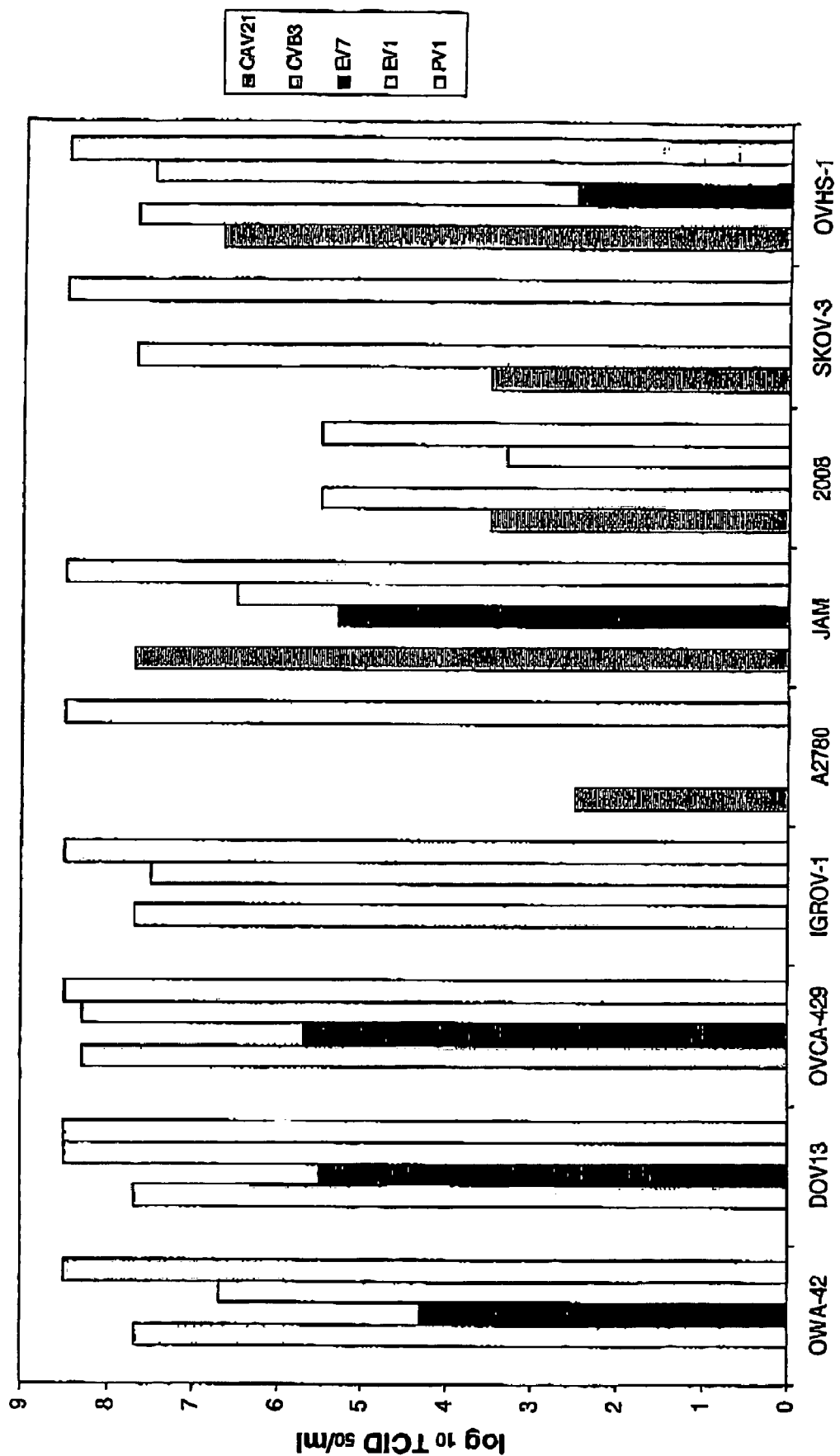
FIG. 8 shows lytic infection of ovarian cancer cells by the enteroviruses CAV21, CVB3, EV1, EV7 and PV1. Fifty percent endpoint titres were calculated and oncolysis was considered significant if the TCID$_{50}$/ml endpoint was $10^4$ or greater.
Figure 9A:
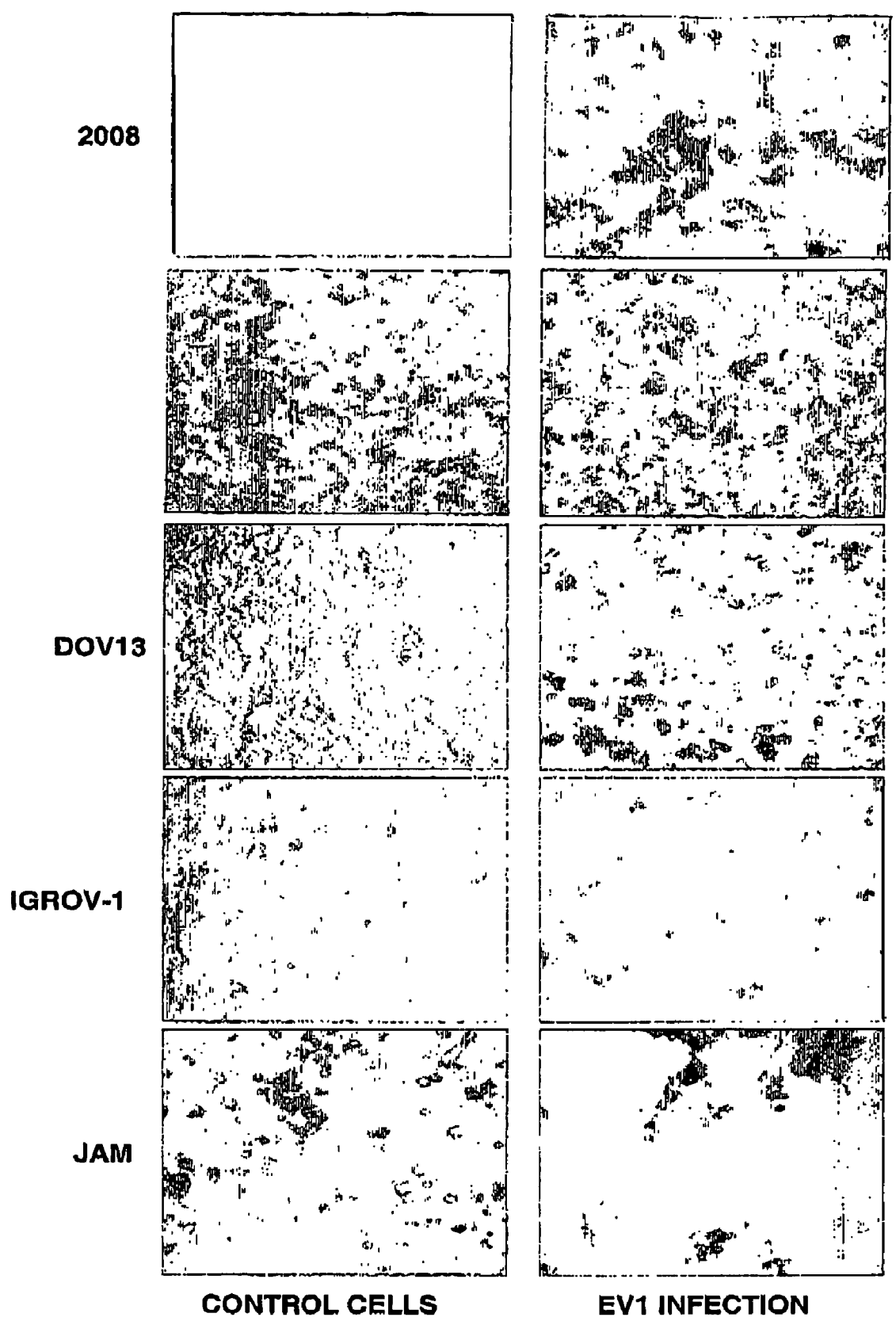
FIG. 9A shows photomicrographs of ovarian cancer cell monolayers infected for 72 hours with a $10^{-1}$ dilution of EV1. At this viral input multiplicity, all cell lines displayed significant levels of oncolysis by EV1 (right) excluding the cell line A2780.
Figure 9B:
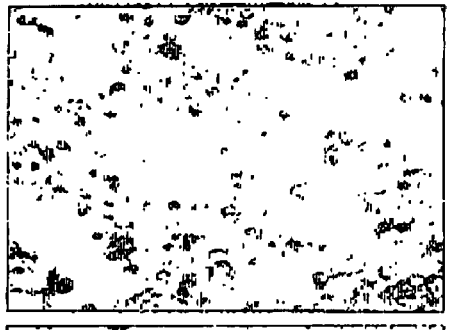
FIG. 9B shows photomicrographs of ovarian cancer cell monolayers infected for 72 hours with a $10^{-1}$ dilution of EV1. All cell lines displayed significant levels of oncolysis by EV1 (right) excluding the cell line SKOV-3.
Figure 9B:
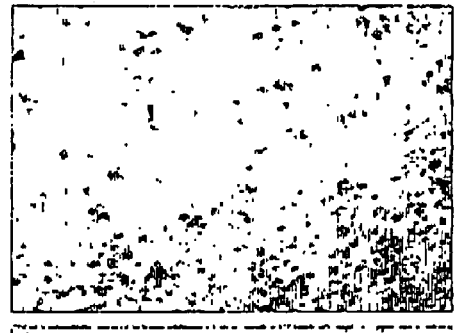
Figure 9B:
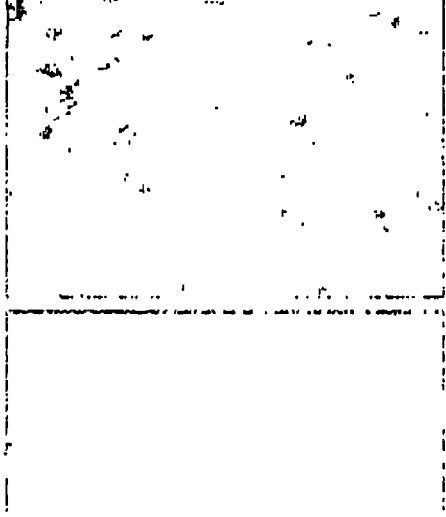
Figure 9B:
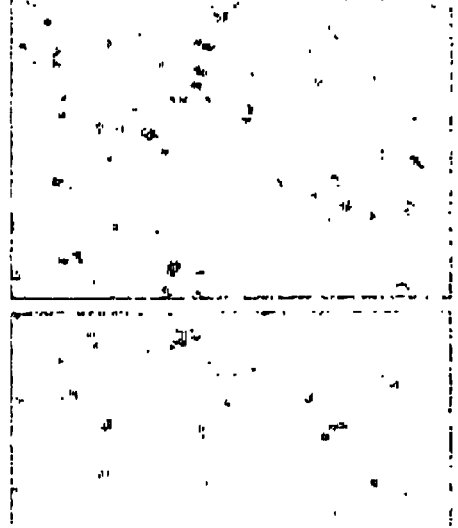
Figure 9B:
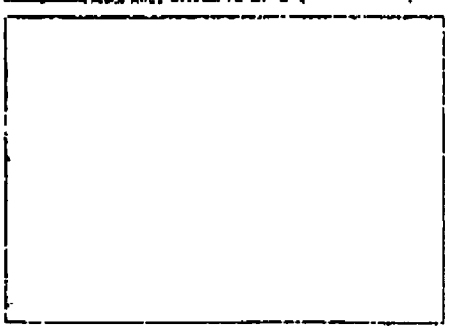
Figure 9B:
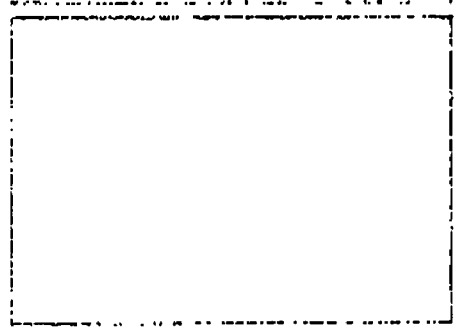
Figure 10:
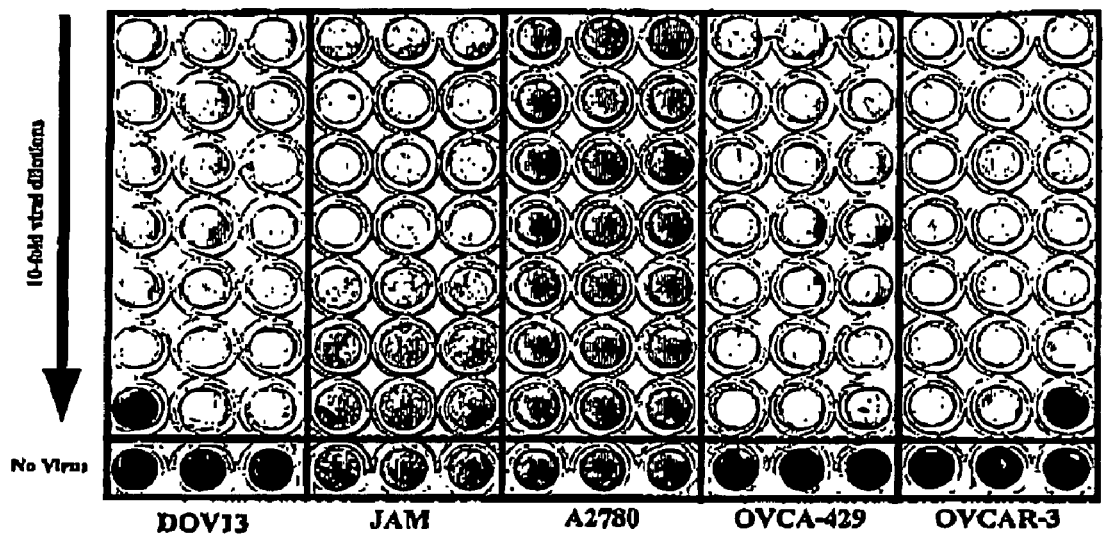
FIG. 10 shows lyric iron of ovarian cancer cells with EV1. Seven of the ten cell lines are considered to be susceptible to oncolysis by EV1. Oncolysis was considered to be significant if a viral titre (TCID$_{50}$/ml) was calculated to be $10^4$ or greater.
Figure 10:
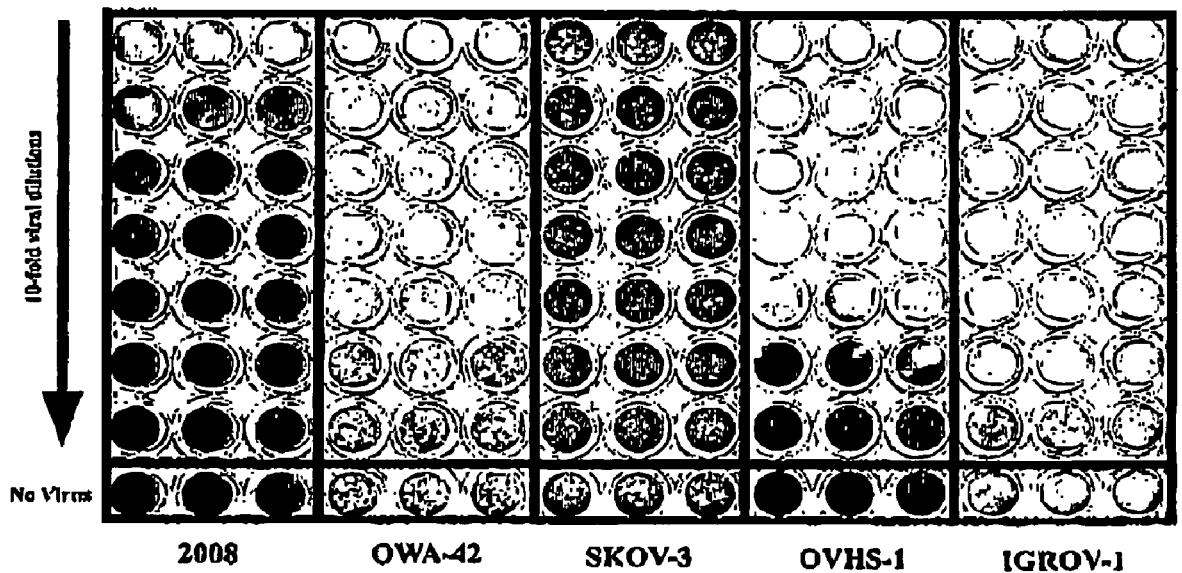

The oncolytic capacity of CAV21, CVB3, EV1, EV7 and PV1 was assessed in each of the nine ovarian cancer cell lines (FIG. 8). CAV21 susceptibility was discovered on two of the nine cell lines while CVB3 caused significant lysis in seven of the nine lines. Ovarian cancers seemed particularly susceptible to echoviruses with EV7 causing death in four of the nine cancer cell lines and EV1 causing seven of the ten cell lines to lyse significantly upon infection (FIGS. 9A, 9B and 10). Vulnerability to PV1 was revealed across all nine ovarian cancer cell lines. Photomicrographs were taken of all ten lines infected with EV1 (FIGS. 9A and 9B) and a microtitre plate lytic infection of the ten ovarian cancer cell lines with EV1 was also observed (FIG. 10).

2.9 Binding of EV1 to Ovarian Cancer Cell Lines

Figure 11:
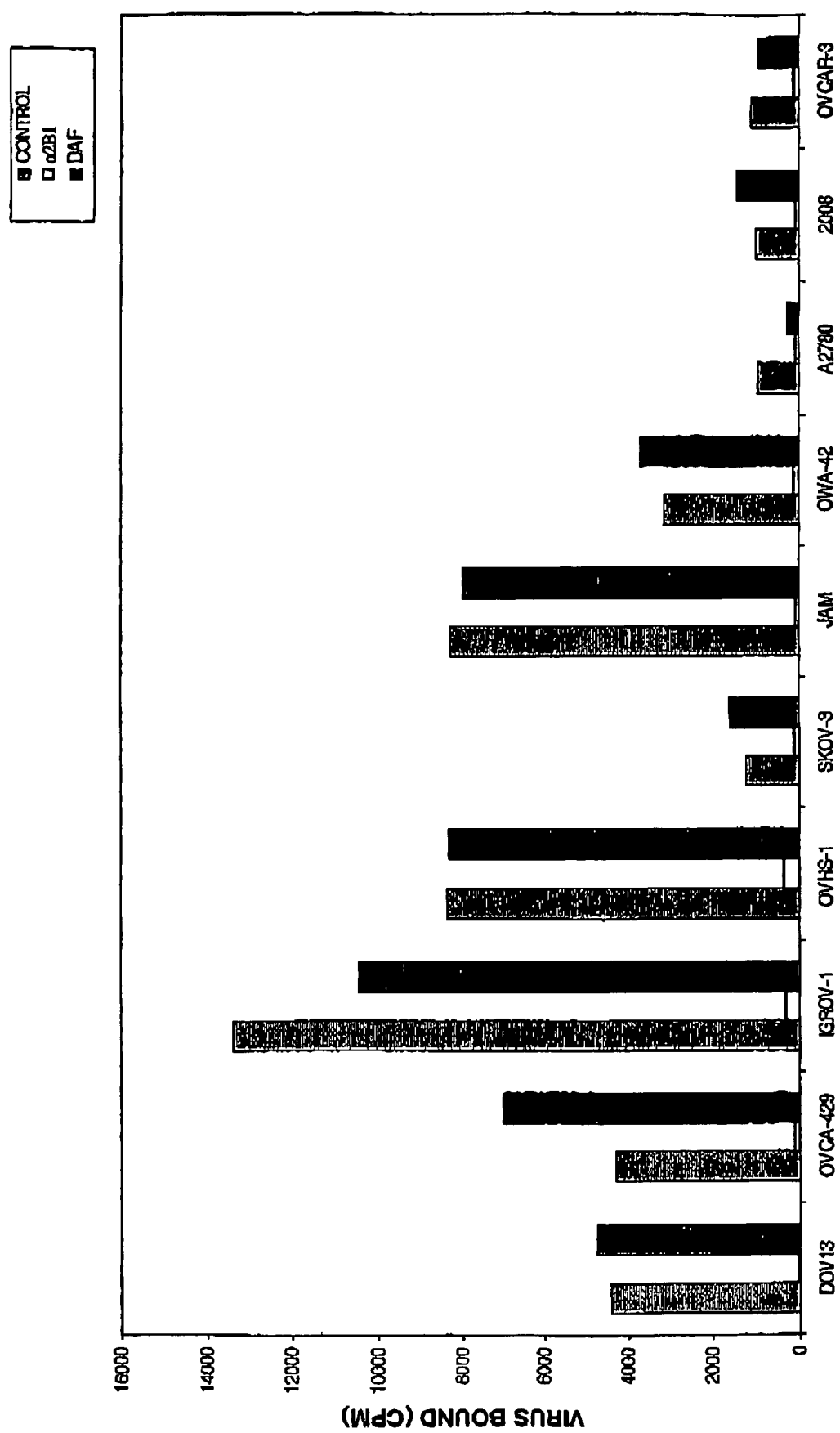
FIG. 11 shows EV1 binding inhibited in the presence of anti-$\alpha_2\beta_1$. Binding of [$^{35}$S]-methionine labeled EV1 to ovarian cancer cell lines in the presence and absence of either anti-$\alpha_2\beta_1$ or anti-DAF MAbs. Levels of [$^{35}$S]-methionine labeled virus bound was determined by liquid scintillation counting on a 1450 MICROBETA® TRILUX (Wallac, Finland).

As ovarian cancer cell lines were highly susceptible to oncolysis by EV1 further investigations to evaluate the nature of EV1 cell attachment were undertaken. Cells were preincubated with either anti-$\alpha_2\beta_1$ (AK7) or anti-DAF (VIIIA7) monoclonal antibodies before radiolabeled EV1 was added to determine the involvement of these receptors in EV1 host cell binding. Binding of EV1 was apparent on all ten of the cell lines tested. By blocking the $\alpha_2\beta_1$ integrin with anti-receptor antibody cellular attachment of EV1 was significantly inhibited. Blocking of the cell surface receptor DAF with the monoclonal antibody VIIIA7 caused no significant inhibition of EV1 binding (FIG. 11).

Figure 12:
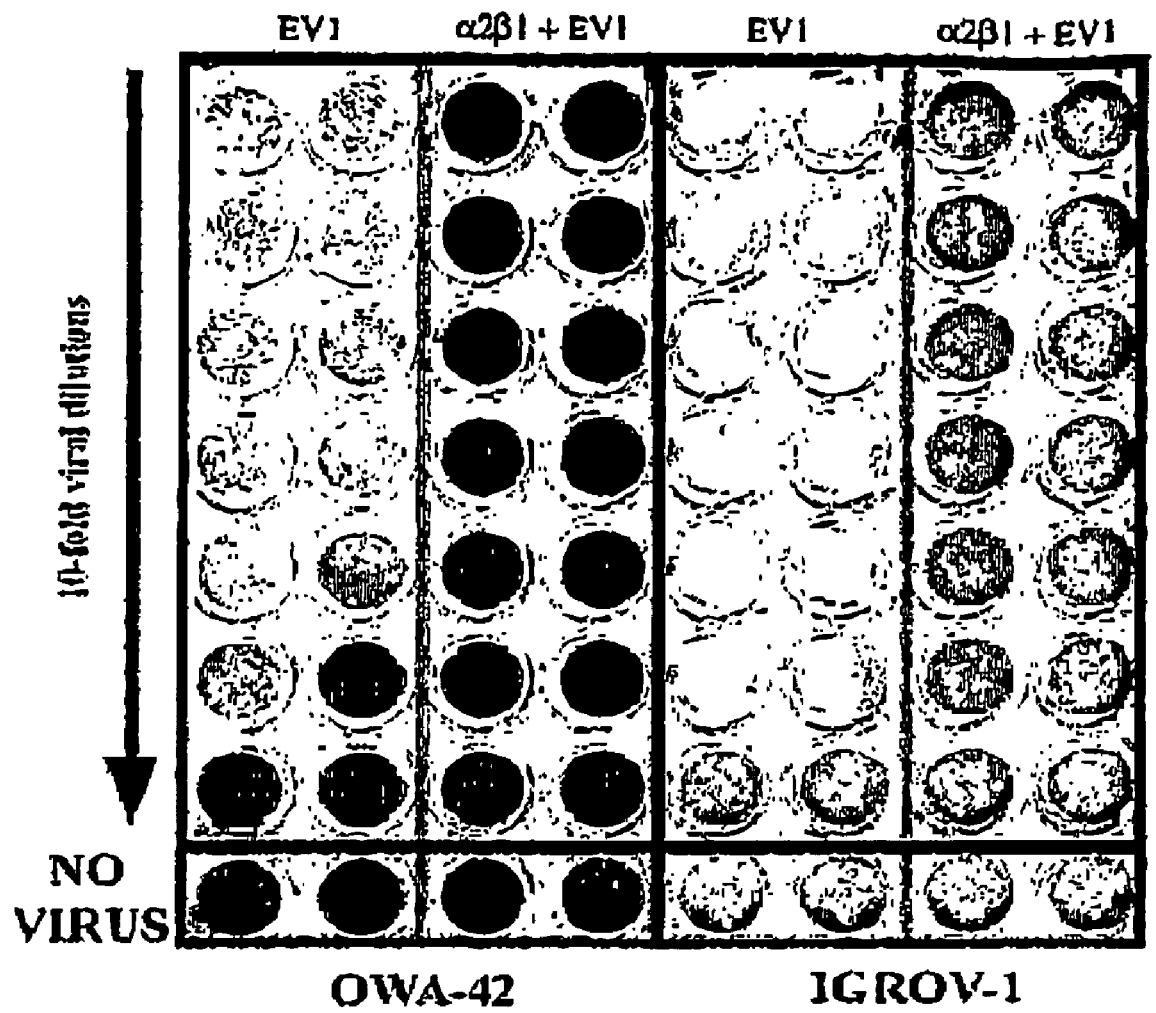
FIG. 12 shows lytic infection of the ovarian cancer cell lines OWA-42 and IGROV-1 by EV1 in the presence or absence of anti-$\alpha_2\beta_1$ MAb. 72 hours post infection the cells preincubated with the anti-$\alpha_2\beta_1$ MAb remained completely protected. Cell survival was determined by staining with crystal violet methanol solution.
Figure 13:
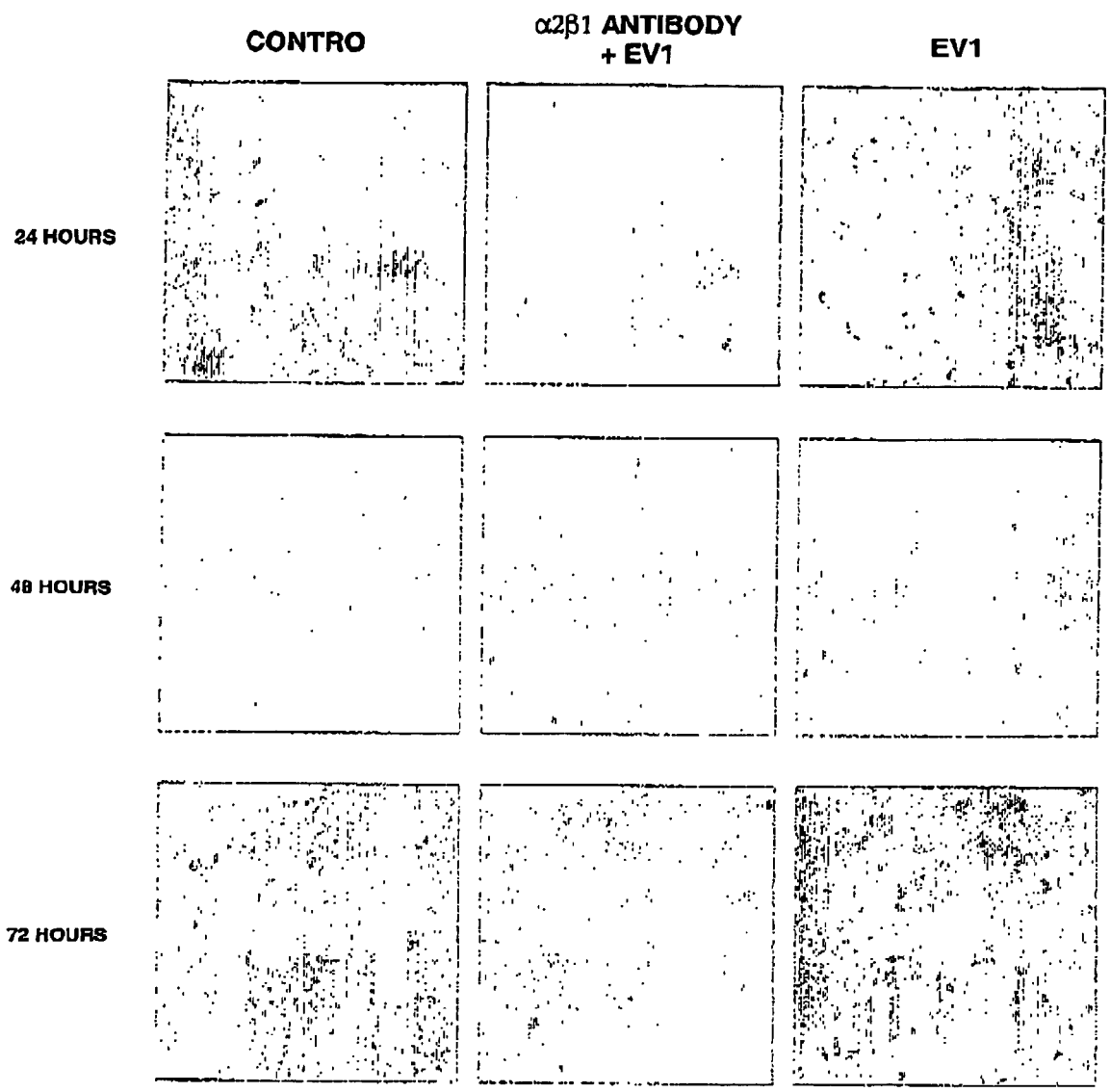
FIG. 13 shows lytic infection of OWA-42 ovarian cancer cell monolayers by EV1 in the presence or absence of anti-$\alpha_2\beta_1$ MAb. Photomicrographs were taken at 24, 48 and 72 hours post infection demonstrating the complete protection of the cells from EV1 infection due to the monoclonal antibody blockade of the $\alpha_2\beta_1$ receptor.

2.10 Antibody Blockade of $\alpha_2\beta_1$ Integrin Inhibits EV1 Infection of Ovarian Cancer Cell Lines In order to assess the function of $\alpha_2\beta_1$ in EV1 infection, a lytic assay was performed where the cell monolayer was preincubated with anti-$\alpha_2\beta_1$ (AK7) monoclonal antibody. OWA-42 and IGROV-1 ovarian cancer cell lines were analysed. After 72 hours post virus infection the cell monolayers in the absence of MAb blockade were highly susceptible to EV1 lytic infection. Following MAb blockade of the $\alpha_2\beta_1$ integrin there was no indication of oncolysis in the cell lines even at the lowest dilution of EV1 (FIG. 12). Photomicrographs were taken at 24, 48 and 72 hours post infection of the OWA-42 cell line (FIG. 13).

2.11 Non-Cancerous Human Cells Not Susceptible to EV1 Infection

Figure 14:
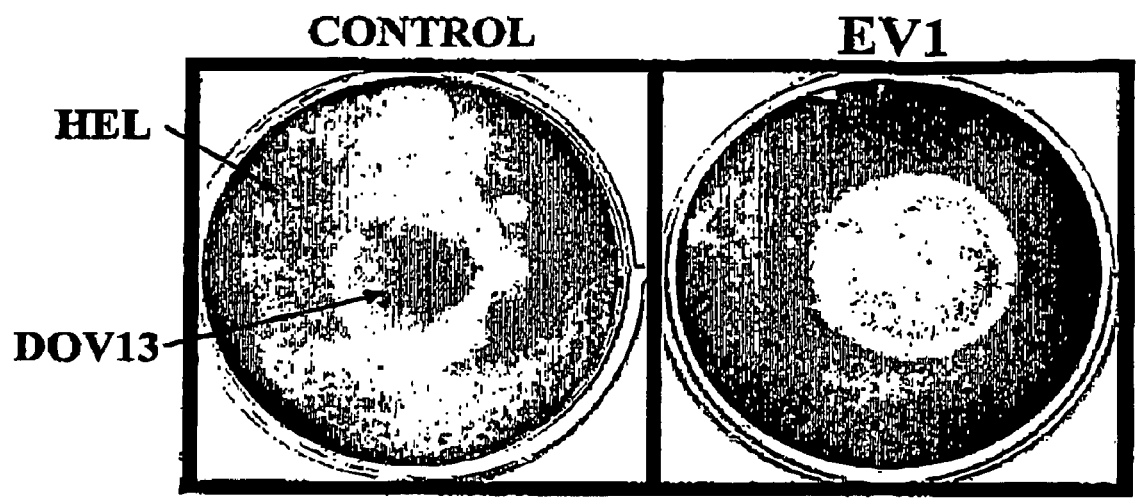
FIG. 14 shows DOV13 ovarian cancer cells were cultured within the ring insert and HeLa cells (human fibroblast cells) were cultured in the outer ring. Post infection with EV1 the viable cells were stained with crystal violet methanol solution. EV1 specifically infected the ovarian cancer cells while the HeLa cells remained healthy.

An experiment was performed to examine the effect that EV1 has on non-cancerous human cells, determined by infecting human fibroblast with EV1. Briefly, 6-well tissue culture plates were prepared with a tissue culture ring insert, DOV13 cells within the ring and HeLa cells, human fibroblasts (obtained from CSL, Australia), in the outer ring incubated at 37° C. until confluent monolayers were formed. The ring was removed and cells were infected with EV1 overnight at 37° C. Viable cells were stained with crystal violet methanol solution Upon infection with EV1 the DOV13 ovarian cancer cells were lysed whereas the HeLa cells remained healthy (FIG. 14) demonstrating the specific susceptibility of the ovarian cancer cells to EV1.

2.12 Expression of $\alpha_2\beta_1$ on Melanoma Cell Line SkMel28

Figure 15:
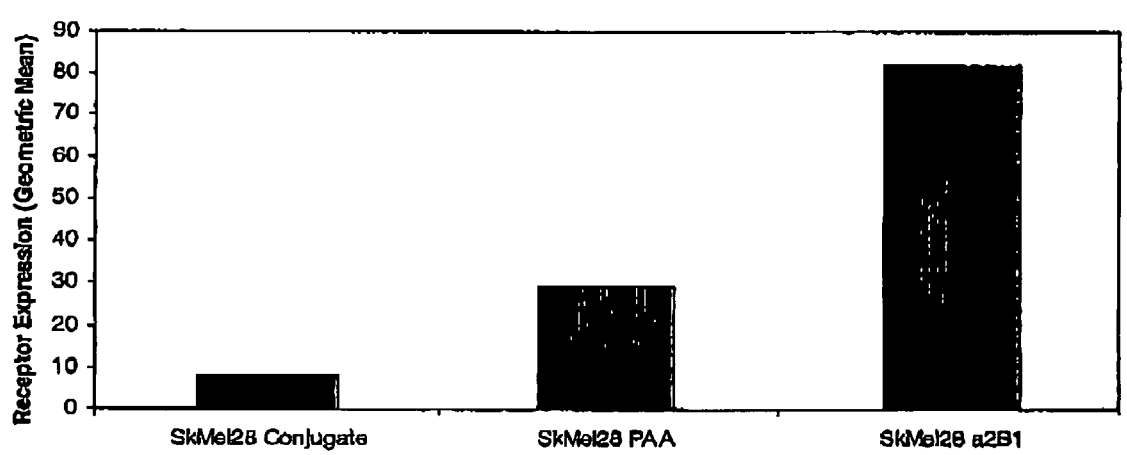
FIG. 15 shows flow cytometric analysis of the level of surface expressed $\alpha_2\beta_1$ on the melanoma cell line SkMel28. SkMel28 cells were incubated with R-phycoerythrin-conjugated $F(ab')_2$ fragment of goat anti-mouse immunoglobulin in the presence or absence of anti-$\alpha_2\beta_1$. The geometric mean of the conjugate sample was subtracted from the geometric mean of the sample detaining the shift and thus the expression of the receptor. Significant $\alpha_2\beta_1$ expression is demonstrated due to the shift in geometric mean.

Melanomas, cancer of the skin are known to up regulate $\alpha_2\beta_1$ expression. The melanoma cell line SkMel28 was examined for expression using flow cytometry. High levels of $\alpha_2\beta_1$ expression were observed. However, a low background level of binding was exhibited by the control MAb (FIG. 15).

2.13 Binding of EV1 to SkMel28

Figure 16:
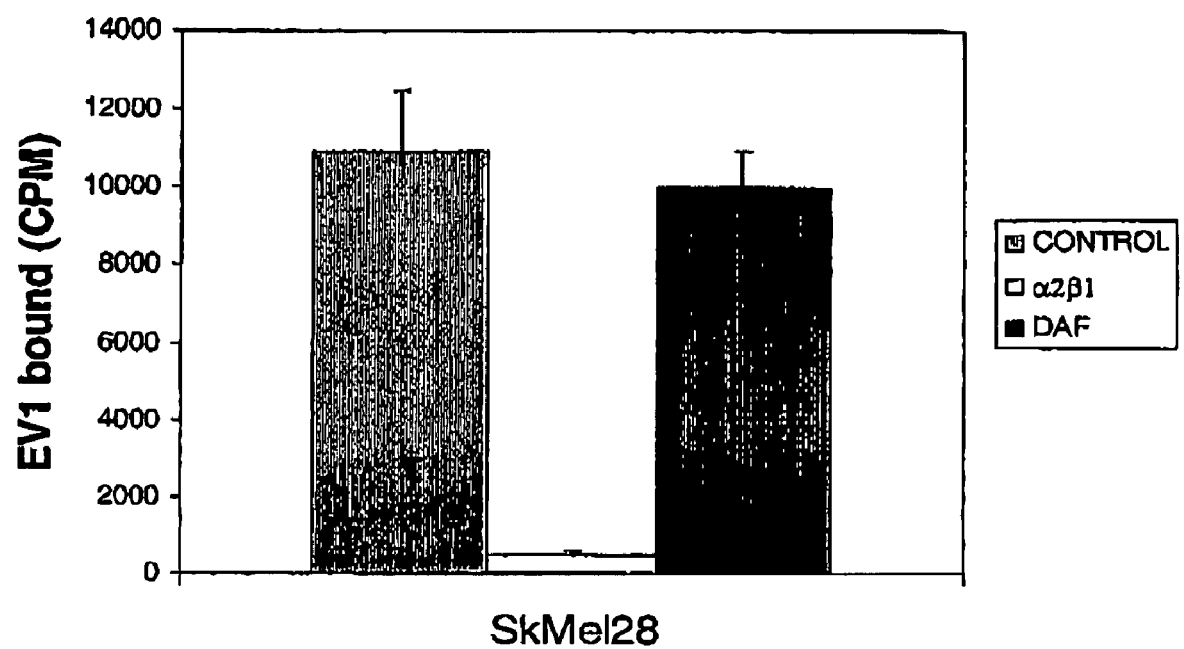
FIG. 16 shows binding of [$^{35}$S]-methionine labeled EV1 to SkMel28 melanoma cells in the presence and absence of either anti-$\alpha_2\beta_1$ or anti-DAF MAbs. Levels of [$^{35}$S]-methionine labeled virus bound was determined by liquid scintillation counting on a 1450 MICROBETA® TRILUX (Wallac, Finland). $\alpha_2\beta_1$ blockade resulted in significant inhibition of EV1 binding. Results are expressed as the mean of triplicate samples±standard error.

To further investigate the nature of EV1 attachment to surface expressed $\alpha_2\beta_1$ on SkMel28 cells, radiolabeled virus binding assays were undertaken. The radiolabeled EV1 bound significantly to the malignant melanoma cell line with MAb blockade of $\alpha_2\beta_1$ severely depleting the amount of EV1 bound (FIG. 16).

2.14 Infectivity Assay of SkMel28 with EV1

Figure 17:
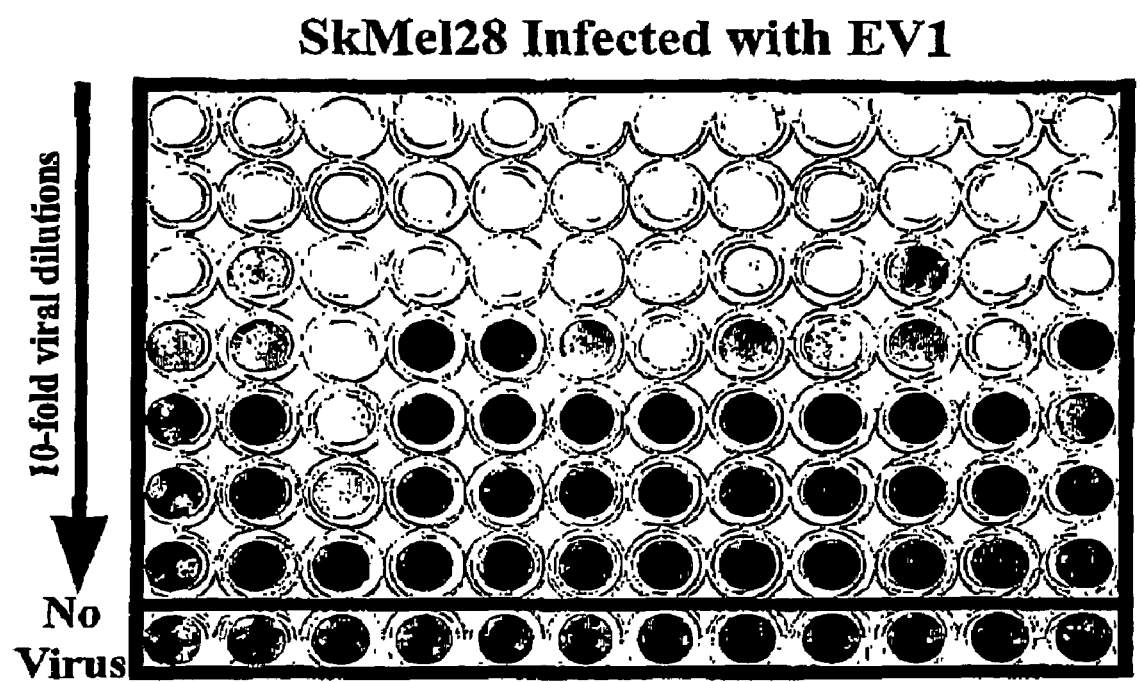
FIG. 17 shows lytic infection of SkMel28 melanoma cells with EV1. Cell survival was determined by crystal violet methanol solution. Significant lysis can be observed.

A lytic infectivity assay was performed to determine the susceptibility of SkMel28 to EV1 infection. The malignant melanoma cell line displayed moderate oncolysis upon infection with EV1. The crystal violet stain was absorbed by cells not undergoing lytic infection where as the non-stained wells represent complete lysis of cell monolayers (FIG. 17).

2.15 Discussion

Ovarian cancer cell lines were found to be highly susceptible to lytic infections by EV1 with seven of the ten cell lines tested showing significant oncolysis. Further studies into the binding of EV1 to the ovarian cancer cell lines confirmed that $\alpha_2\beta_1$ is the primary receptor used by EV1. The radiolabeled binding studies further indicated $\alpha_2\beta_1$ was required for virus binding and the MAb blocking assay revealed that by pre-treating susceptible ovarian cancer cells with an $\alpha_2\beta_1$ monoclonal antibody (Mab), EV1 infection was completely inhibited. The DAF MAb VIIIA7 was also used in the binding assay as a negative control treatment to determine if DAF played a role in EV1 binding as it does with the enteroviruses CAV21 and CVB3. No significant blockage of EV1 binding occurred with anti-DAF MAb pre-treatment.

Co-culturing ovarian cancer cells with human fibroblasts followed by EV1 infection revealed that human fibroblast cells were not susceptible to EV1 infection even in an environment where the virus specifically lysed the ovarian cancer cells.

The effect of EV1 mediated oncolysis on a melanoma cell line was also investigated. The data revealed that $\alpha_2\beta_1$ was up regulated on the surface of the SkMel28 melanoma cell line and that these cells were susceptible to EV1 lytic infection. The binding of EV1 to the ovarian cancer cells was shown to be via $\alpha_2\beta_1$ interactions as shown by the radiolabeled binding assay. The remaining cancer cell lines that were permissive for EV1 infection were colon cancer cell lines with three of the four cell lines highly susceptible as well as both prostate cancer cell lines. Both these cancer types may encounter the same extracellular matrix as ovarian cancer cells and hence, upregulate their $\alpha_2\beta_1$ expression during metastasis through extracellular matrix rich in collagen I found on peritoneal surfaces.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLE 3

Specificity of Echovirus (EV2) Lytic Infection 3.1 Relative Pathogenicity of EV1

The relative pathogenicity of EV1 on in vitro cultures of non-malignant ovarian cells compared to neoplastic cells was investigated. Normal human ovarian surface epithelial (HOSE) cells immortalised using human papillomavirus 16 E6-E7 open reading frames (Tsao, S. W. et al., 1995), together with a dear cell ovarian carcinoma line (OVHS-1) and undifferentiated ovarian carcinoma cells (DOV13) were challenged with input multiplicities of EV1 ranging from moi 5.0 to 0.05 $TCID_{50}$/cell. At 48 h post-infection microscopic examination revealed gross cell destruction and cytolysis in monolayers of both ovarian carcinoma lines, even at a viral challenge of as low as 0.05 $TCID_{50}$ of EV1 per cell. In contrast, no detectable changes in the cell morphology of the HOSE cells were observed even at the highest viral challenge dose.

In a further effort to the deter e the specificity of the EV1 infection, normal peripheral blood lymphocytes (PBLs) as well as OVHS-1 and DOV13 cells were challenged with EV1 (moi=1.0). Flow cytometric analysis revealed that PBL cell preparation expressed little to no surface $\alpha 2\beta 1$, while both ovarian cancer cell lines expressed high levels of $\alpha 2\beta 1$. EV1-mediated cytolysis of suspensions of PBLs and ovarian cancer cells was assessed by using a standard cell cytotoxicity assay meaning the release of LDH. EV1 challenge resulted in almost complete cell cytolysis of the ovarian cultures by EV1 infection, while only background levels of cytolysis were observed in the PBLs following exposure to the same input dose of EV1.

To determine whether EV1 initiated a productive infection in PBLs in the absence of detectable cell lysis and to confirm that the background level of cytolysis was non-specific and not mediated by EV1 infection, suspension of PBLs and two ovarian carcinoma lines were inoculated with EV1 (moi=1.0) and monitored for the production of progeny virus. In both ovarian cancer cell lines (OVHS-1 and DOV-13) EV1 titers increased by approximately $10^4$-fold over the initial cell bound inoculum. In contrast, no progeny virus was produced by the PBLs over the 48 h incubation period with the observed infectivity consisting non-specifically bound residual input inoculum.

EXAMPLE 4

Figure 18:
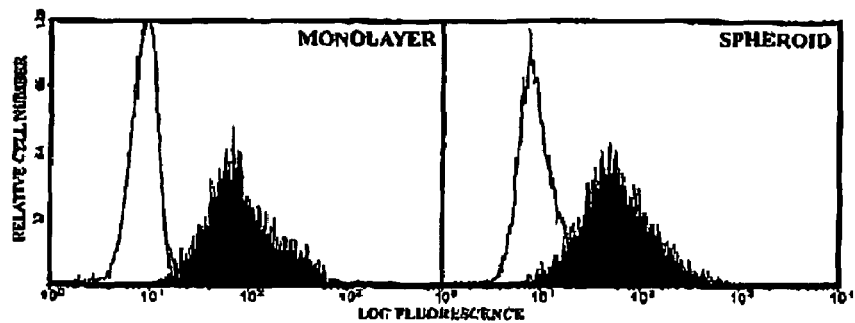
FIG. 18 is a photomicrograph showing treatment of ovarian cancer multi-cell spheroids with EV1.
Figure 18:
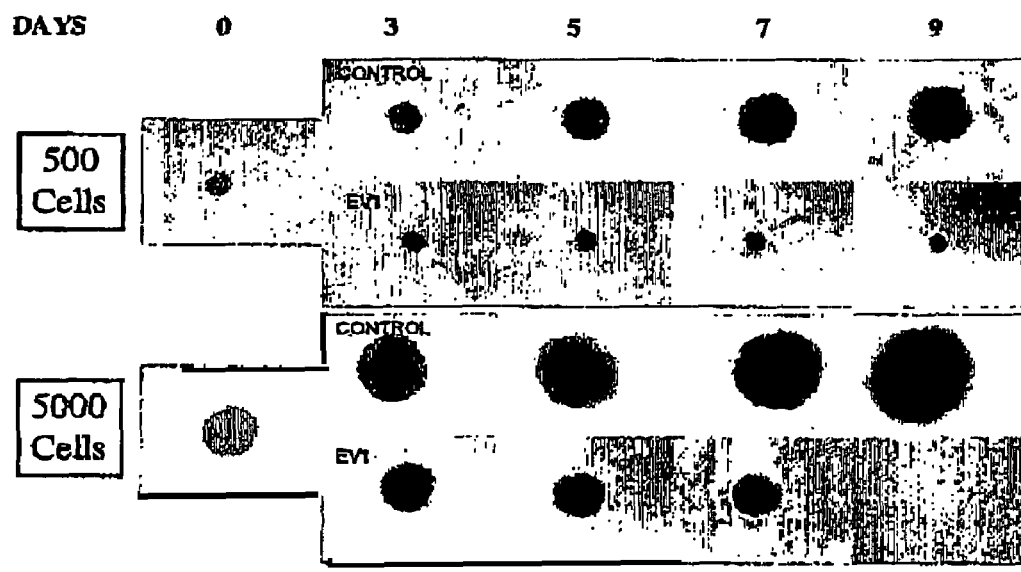

Echovirus (EV1) Lysis of Ovarian Cancer Cells 4.1 EV1 Lysis of in vitro Cultured Ovarian Cancer Cell Spheroids Many in vitro cultures of ovarian cancer cells can be propagated as multi-dimensional spheriods (Casey, R. C et al., 2001). Multi-cell spheriods simulate the multicellular aggregates commonly found in the ascitic fluid of patients with advanced stage ovarian carcinoma. Having established that monolayer cultures of ovarian are highly susceptible to lytic infection by EV1, multi-ovarian cancer cell spheriods were challenged with EV1. Flow cytometric analysis determined that the surface expression levels of the EV1 cellular receptor, $\alpha 2\beta 1$ were comparable, whether OVHS-1 cells were grown in monolayer or spheriod formation. EV1 ($10^5$ $TCID_{50}$) was administered to the semi-solid agarose media surrounding the spheriods with photomicroscopic images of the spheroid morphology obtained at various intervals post-viral challenge. FIG. 18 shows that the control non-infected spheriods were actively proliferating, resulting in steadily increases in volume throughout the 9 day incubation period. In contrast EV1 infected spheriods exhibited slight decreases in volume during the first 7 days post inoculation, with significant structural desegregation and cellular destruction occurring over the next 48 h. The data shows EV1 initiates a productive cell to cell lyric infection within the cancerous spheriod which is effective in retarding spheriod growth regardless of the initial pre-inoculation spheriod volume (ie $5\times10^2$ or $5\times10^9$ cells).

4.2 Effect of Echovirus 1 on an Ascites Model of Human Ovarian Cancer

In the late stages of metastatic ovarian cancer, the tumor cells migrate throughout the peritoneal cavity and/or colonise distant tissue sites. To determine whether EV1-mediated oncolysis is an effective therapy for advanced stages of peritoneal ovarian cancer, a SCID-mouse ascites model bearing human ovarian carcinoma xenografts was employed. SCID mice were injected via the intraperitoneal route with $2\times10^6$ OVHS-1 cells 14 days before the administration of live EV1. The experimental treatment regime consisted of a single dose of either PBS, UV-inactivated EV1 or live EV1 ($10^5$ $TCID_{50}$)

injected via the intraperitoneal route. Changes in the body weight of mice receiving the various treatments relative to those of mice not bearing ovarian cancer xenografts were used as a marker of the development of ascites burden.

Figure 19A:
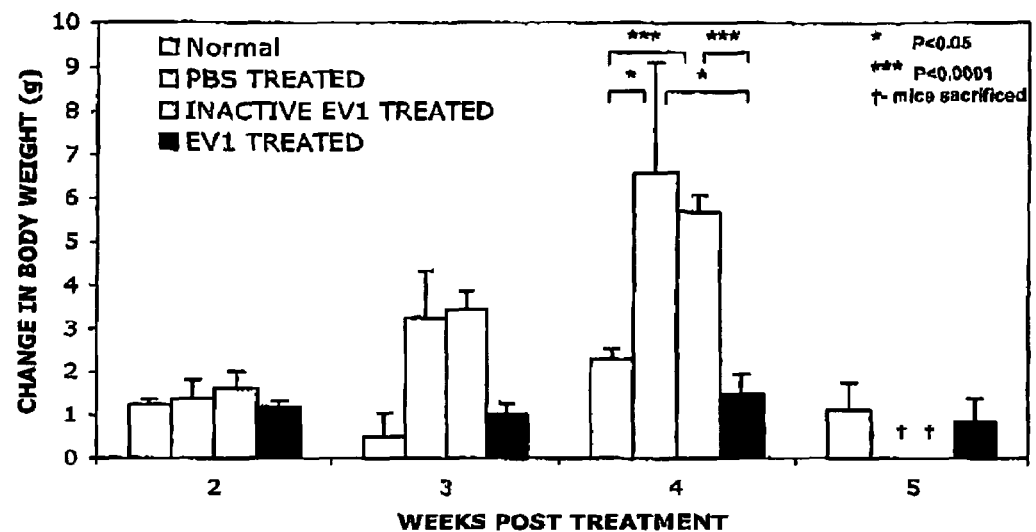
FIG. 19A is a histogram showing change in body weight of SCID-mice administered with $1.0\times10^6$ OVHS-1 cells via the intraperitoneal (i.p) route 3 weeks prior to injection with either phosphate buffered saline (PBS), UV-inactivated Echovirus EV1 or infectious EV1 ($10^5$ $TCID_{50}$) by the i.p. route.
Figure 19B:
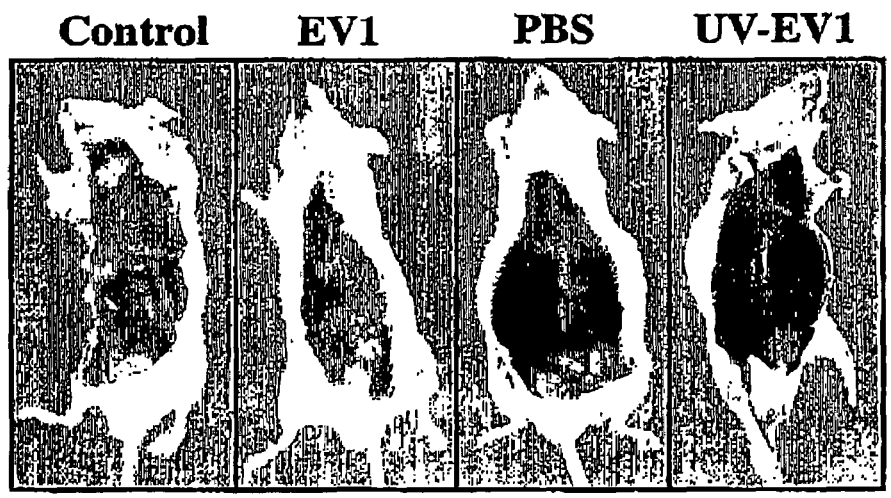
FIG. 19B shows photographs taken 5 weeks post-injection of a normal control SCID-mouse compared to mice injected with the OVHS-1 cells and treated with PBS, UV-inactivated EV1 or EV1. Note the development of peritoneal ascites in tumor bearing mice administered PBS or UV-inactivated EV1.

At 3 weeks post-treatment nice administered PBS or UV-inactivated EV1 exhibited significant increases in weight but no difference between the normal and EV1 treated mice was observed. The body weight of the PBS or UV-inactivated EV1 groups continued to rise and at 4 weeks PI substantial abdominal swelling due to accumulation of ascites fluid was evident in all mice but not in the remaining treatment group (FIG. 19A). At 5 weeks PI, all mice from the PBS and UV-inactivated EV1 were sacrificed due to excessive peritoneal ascites, while no detectable weight gain or ascites formation was observed between the EV1-treated mice and animals that did not receive ovarian cancer xenografts (FIG. 19B). Throughout the course of this investigation no signs of dramatic disease development were observed in mice injected with live EV1, even in the presence of serum viral loads 10-100 fold (at 7-14 days PI; data not shown) in excess of the viral inoculum dose.

4.3 Discussion

One of the major requirements for a successful viral oncolytic strategy using replication-competent viruses is low viral pathogenicity for the host but a high predilection for neoplastic cells.

In the present study the capacity of representative human echoviruses to induce lytic infection of in vitro cell cultures of human ovarian cancer cells was assessed. Despite, being highly oncolytic for melanoma cells, CVA21 and a prototype strain of EV7 were not as potent as EV1 at inducing productive lytic infections in a number of human ovarian cancer cell monolayers. Monoclonal antibody blocking studies confirmed that the EV1-mediated lytic infection of ovarian cancer cells was initiated via specific viral capsid binding with cell surface expressed inter $\alpha2\beta1$. As integrin $\alpha_2\beta_1$ does not permit simultaneously binding of both EV1 and collagen, EV1 lytic infection of ovarian cancer cells not only mediates rapid cell oncolysis, but may also interfere with interactions between with type 1 collagen and $\alpha2\beta1$ integrin thereby potentially reducing the dissemination of the cancer cell across the peritoneal surface.

Destruction of multi-cellular three dimensional spheroids by EV1 challenge reflects utility of EV1-mediated oncolysis in the in vivo reduction of solid ovarian tumor burden. This efficient lysis of ovarian spheroids by EV1 is impressive considering that individual cells in ovarian spheroids appear to be more robust than cells in monolayer formation, possessing enhanced resistance to radiation and chemical induced apoptosis (Frankel, A. et al., 1997).

Therapeutic oncolytic viruses should possess a discriminatory mechanism for the targeting of malignant cells. Selective EV1-mediated infection was highlighted by the inability of EV1 to induce dramatic cytolysis of a normal epithelial ovarian cell line and peripheral blood lymphocytes (PBLs). The production of high titers of progeny virus from the ovarian cancer cells but not from suspensions of PBLs reinforces the specificity and low pathogenic nature of EV1 infection non-neoplastic cells.

In addition to ovarian carcinomas, malignant melanomas cells also express up-regulated levels of surface integrin $\alpha_2\beta_1$ thereby rendering them susceptible to EV1 challenge. In somewhat of a paradox, EV1 infection of ovarian cancer cells induces increased surface expression of ICAM-1 (Pietiainen, V. et al., 2000), the cell targeting receptor for CVA21 on melanoma cells. Accordingly, challenge of ovarian cancer and/or melanoma malignancies by a therapeutic preparation containing both live EV1 and CVA21 may result in more potent oncolytic infections.

Intraperitoneal administration of EV1 was very effective in controlling the development of ovarian tumor xenografts in the peritoneal cavity of SCID-mice. All mice injected with live EV1 failed to display increased weight gain (relative to mice not injected with ovarian cancer xenografts) and the development of detectable peritoneal ascites. Progeny EV1 generated by in vivo lytic infection of the neoplastic ovarian cells was detected in the blood of mice at 7 days PI (data not shown). Vireamic EV1 can be viewed as an attractive reservoir for the control of de ted disease and its detection at significant levels (approximately $10^6$ $TCID_{50}$) also indicates tat the viral input dose of $10^5$ $TCID_{50}$ may be significantly reduced while maintaining oncolytic potency. The failure to detect vireamic EV1 at 7 days PI in mice not bearing ovarian cancer xenografts (data not shown) suggests that in the absence of susceptible neoplastic cells EV1 is rapidly and effective clearing from systemic circulation.

Overall, the results highlight that EV1 oncolytic therapy is very effective in vitro and in vivo for the control of peritoneal ovarian cancers. The use of the relatively non-invasive EV1 therapy may be viewed as an attractive alternative to current treatment regimes that involve surgical debulking followed by combination chemotherapy. EV1 therapy may also be employed as adjuvant therapy following tumor debulking operations, focussing on the targeting and destruction of neoplastic cells released during the mechanics of surgery. EV1 oncolytic therapy may also be used as a novel therapeutic in the treatment of other human malignancies expressing high levels of integrin $\alpha2\beta1$. Moreover, as EV1 and EV8 compete for the same binding epitope on integrin $\alpha2\beta1$, EV8 may be an alternate choice to EV1 for inducing rapid lytic infections of ovarian carcinoma cells. The availability of two distinct viral serotypes allows sequential challenge of ovarian carcinomas via integrin $\alpha2\beta1$ targeting, independent of a protective immune response generated as a result of the primary viral administration. The availability of a potent anti-enteroviral drug (pleconaril) for EV1 (Pevear, D. C. et al, 1999) further enhances the attractiveness of this therapy, as it affords direct control of non-specific viral replication and disseminated progeny virus. The potential synergy between pleconaril and EV1 may also permit the systemic injection of very high viral input multiplicities followed by administration of pleconaril (to inactivate free virus) shortly after the virus has targeted and commenced lytic infection of the malignant cells.

It will be appreciated by persons skilled in the art that numerous variations and/or modifications may be made to the invention as shown in the specific embodiments without departing from the spirit or scope of the invention as broadly described. The present embodiments are, therefore, to be considered all respects as illustrative and not restrictive.

REFERENCES

1. Andreansky S S, He B, Gillespie G Y, Soroceanu L, Markert J, Chou J, Roizman B and Whitley R J (1996). *The application of genetically engineered herpes simplex viruses to the treatment of experimental brain tumors*. Proc Natl Acad Sci USA 93:11313-8.
2. Ansardi, D. C., Porter, D. C., Jackson, G., Gillespie, Y. and Morrow, C. D. RNA replicons derived from poliovirus are directly oncolytic for human tumor cells of diverse orgins. Cancer Res, 2001, 61:8470-8479.

3. Bartolazzi, A., J. Kaczmarek, G. Nicolo, A. M. Risso, G. Tarone, P. Rossino, P. Defilippi, and P. Castellani, Localization of the alpha 3 beta 1 integrin in some common epithelial tumors of the ovary and in normal equivalents. Anticancer Res, 1993. 13(1): p. 1-11.
4. Bergelson, J. M., B. M. Char, R. W. Finberg, and M. E. Hemler, The integrin VLA-2 binds echovirus 1 and extracellular matrix ligands by different mechanisms. J Clin Invest 1993. 92(1): p. 232-9.
5. Cannistra, S. A., C. Ottensmeier, J. Niloff, B. Orta, and J. DiCarlo, Expression and function of beta 1 and alpha v beta 3 integrins in ovarian cancer. Gynecol Oncol, 1995. 58(2): p. 216-25.
6. Cardarelli, P. M., S. Yamagata, I. Taguchi, F. Gorcsan, S. L. Chiang, and T. Lobl, The collagen receptor alpha 2 beta 1, from MG-63 and HT1080 cells, interacts with a cyclic RGD peptide. J Biol Chem, 1992. 267(32): p. 23159-64.
7. Casey, R. C. et al, (2001), Beta 1-integrins regulate the formation and adhesion of ovarian carcinoma multicellular spheroids. Am J Pathol. 159:2071-80.
8. Chan, B. M., N. Matsuura, Y. Takada, B. R. Zetter, and M. E. Hemler, In vitro and in vivo consequences of VLA-2 expression on rhabdomyosarcoma cells. Science, 1991. 251(2001): p. 1600-2.
9. Fenner, F. et al., The Biology of Animal Viruses. Academic Press. New York, 1974 Second Edition.
10. Fields, B. N. and D. M. Knipe, Fields Virology. 4th Edition ed. Vol. 1. 2000, New York: Raven Press.
11. Flint, S. J. et al., 2000, Principles of Virology: Molecular Biology, pathogenesis and control, ASM Press, Washington.
12. Frankel, A. et al., (1997), Abrogation of taxol-induced G2-M arrest and apoptosis in human ovarian cancer cells grown as multicellular tumor spheroids. Cancer Res. 57:2388-93.
13. Harris, R. E. and Pindak, F. F. (1975). Viral replication in human ovarial cell culture. Gynecol. 46(2):227-230.
14. He, T. C., A simplified system for generating recombinant adenoviruses. Proc, Natl. Acad, Sci. USA, 1998, 95:2509-2514
15. Kamata, T. and Y. Takada, Direct binding of collagen to the I domain of integrin alpha 2 beta 1 (VLA-2, CD49b/CD29) in a divalent cation-independent manner. J Biol Chem, 1994. 269(42): p. 26006-10.
16. Kramer, R. H. and N. Marks, Identification of integrin collagen receptors on human melanoma cells. J Biol Chem, 1989. 264(8): p. 4684-8.
17. McCracken, A. W. and K. M. Wilkie, Epidemic pleurodynia in Aden associated with infection by echovirus type 1. Trans R Soc Trop Med Hyg, 1969. 63(1): p. 85-8.
18 Moser, T. L., S. V. Pizzo, L. M. Bafetti, D. A. Fishman, and M. S. Stack, Evidence for preferential adhesion of ovarian epithelial carcinoma cells to type I collagen mediated by the alpha2beta1 integrin. Int J Cancer, 1996. 67(5): p. 695-701.
19. Natalie P G, Hamby C V, Felding-Habermann B, Liang B, Nicotra M R, Di Filippo F, Giannarelli D, Temponi M, Ferrone S (1997). *Clinical significance of alpha(v) beta3integrin and intercellular adhesion molecule-1 expression in cutaneous malignant melanoma lesions.* Cancer Res. April 15; 57(8):1554-60.
20. Nemunaitis J (1999). *Oncolytic virus.* Investigational New Drugs 17:375-386
21. Pietianen, V. et al., (2000). Effects of echovirus 1 infection on cellular gene expression. Virology. 276:253-50
22. Pevear, D. C. et al., (1999). Activity of pleconaril against enteroviruses. Antimicrob. Agents Chemother. 43:2109-15.
23. Ramos, D M., E. D. Berston, and R. H. Kramer, Analysis of integrin receptors for laminin and type V collagen on metastatic B16 melanoma cells. Cancer Res, 1990. 50(3): p. 72834.
24. Randazzo B P, Kesari S, Gesser R M, Alsop D, Ford J C, Brown S M, Maclean A and Fraser N W (1995). *Treatment of experimental intracranial melanoma with a neuroattenuated herpes simplex virus 1 mutant.* Virology 211:94-101.
25. Reed, L. J. and H. A. Muench, A simple method of estimating fifty percent endpoints. Am J Hyg, 1938. 27: p. 493-497.
26. Rossmann, M. G., J. Bella, P. R. Koltkar, Y. He, E. Wimmer, R. J. Kuhn, and T. S. Baker, Cell recognition and entry by rhino- and enteroviruses. Virology, 2000. 269(2): p. 239-47.
27. Satyamoorthy K, Soballe P W, Soans F and Herlyn M (1997). *Adenovirus infection enhances killing of melanoma cells by a mitotoxin.* Cancer Research 57:1873-1876.
28. Shafren D R, Dorahy D J, Ingham R A, Bums G P and Barry R D (1997). *Coxsackievirus A21 binds to decay-accelerating factor but requires intercellular adhesion molecule 1 for cell entry.* J Virol. June; 71(6):4736-43.
29. Strong J E, Coffey M C, Tang D, Sabinin P and Lee P W K (1998). *The molecular basis of viral oncolysis*: usurpation of the Ras signalling pathway by reovirus. 17(12): 3351-3362
30. Tsao, S. W. et al., (1995). Characterisation of human ovarian surface cells immortalised by human papilloma viral oncogenes (HPV-E6E7 ORFS), Exp Cell Res. 218: 499-507.
31. Xiao, C., C. M. Bator, V. D. Bowman, E. Rieder, Y. He, B. Hebert, J. Bella, T. S. Baker, E. Wimmer, R. J. Kuhn, and M. G. Rossmann, Interaction of coxsackievirus A21 with its cellular receptor, ICAM-1. J Virol, 2001. 75(5): p. 2444-51.
32. Xing, L., Non-enveloped virus infection probed with host cellular molecules: a structural study, in Department of Biosciences. 2002, Karolinska Institutet, Sweden: Stockholm.

The invention claimed is:

1. A method for treating abnormal cells in a mammal comprising administering to the mammal an effective amount of an echovirus, which recognizes integrin $\alpha_2\beta_1$ for infectivity of the cells such that at least one of the cells are killed by the virus, wherein the abnormal cell is a cancer cell expressing $\alpha_2\beta_1$.

2. The method according to claim 1 further comprising subjecting the mammal to more than one treatment with the virus, and wherein the virus in each of the treatments has the same or different serotypes.

3. The method according to claim 1, wherein the virus is EV1 or EV8.

4. The method according to claim 1, wherein the virus is modified to express the peptide motif RGD on its viral capsid surface.

5. The method according to claim 4, wherein the virus maintains the echovirus serotype.

6. The method according to claim 5 wherein the virus is a modified form of EV1 or EV8.

7. The method according to claim 1 wherein the virus is administered to the mammal in combination with a second virus which infects the abnormal cells.

8. The method according to claim 7 wherein the abnormal cells express ICAM-1 and the second virus recognizes ICAM-1 for infectivity of the abnormal cells.

9. The method according to claim 8 wherein the second virus is a Coxsackievirus or a modified form thereof.

10. The method according to claim 9 wherein the Coxsackievirus is a Coxsackievirus serotype selected from A13, A15, A18 and A21.

11. The method according to claim 1 wherein the abnormal cells are cancer cells.

12. The method according to claim 11 wherein the cancer cells are ovarian cancer cells, melanoma cells, prostate cancer cells, breast cancer cells, pancreatic cancer cells, colon cancer cells or colorectal cancer cells, or are cells that have spread from ovarian cancer, melanoma, prostate cancer, breast cancer, pancreatic cancer, colon cancer or colorectal cancer.

13. The method according to claim 1 wherein the abnormal cells have up-regulated expression of integrin $\alpha_2\beta_1$.

14. The method according to claim 1 wherein the virus is administered topically, systemically or intratumorally to the mammal.

15. A method for inducing an immune response in a mammal against abnormal cells expressing integrin $\alpha_2\beta_1$, the method comprising infecting abnormal cells in the mammal with an echovirus, thereby causing lysis of at least one of the cells and inducing an immune response in the mammal against the abnormal cells, wherein the abnormal cell is a cancer cell expressing $\alpha_2\beta_1$.

16. The method according to claim 15, wherein the virus is EV1 or EV8.

17. The method according to claim 15 wherein the virus is modified to express the peptide motif RGD on its viral capsid surface.

18. The method according to claim 17, wherein the virus maintains the echovirus serotype.

19. The method according to claim 17 wherein the modified echovirus is a modified form of EV1 or EV8.

20. The method according to claim 15 wherein the abnormal cells have up-regulated expression of integrin $\alpha_2\beta_1$.

21. The method according to claim 15 wherein the virus is administered to the mammal in combination with a second virus which infects the abnormal cells.

22. The method according to claim 21 wherein the abnormal cells express ICAM-1 and the second virus recognizes ICAM-1 for infectivity of the abnormal cells.

23. The method according to claim 22 wherein the second virus is a Coxsackievirus or modified form thereof.

24. The method according to claim 23 wherein the Coxsackievirus is a Coxsackievirus serotype selected from A13, A15, A18 and A21.

25. The method according to claim 15 wherein the abnormal cells are cancer cells.

26. The method according to claim 25 wherein the cancer cells are ovarian cancer cells, melanoma cells, prostate cancer cells, breast cancer cells, pancreatic cancer cells, colon cancer cells or colorectal cancer cells, or are cells that have spread from ovarian cancer, melanoma, prostate cancer, breast cancer, pancreatic cancer, colon cancer or colorectal cancer.

27. The method according to claim 15 wherein the virus is administered topically, systemically or intratumorally to the mammal.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial sequence
```

```
<220> FEATURE:
<223> OTHER INFORMATION: Primer

<400> SEQUENCE: 1
caagacaggg accaaagagg at                                              22

<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2
ccactcgcct ggttgtaatc a                                               21

<210> SEQ ID NO 3
<211> LENGTH: 18
<212> TYPE: DNA
<213> ORGANISM: Artificial sequence
<220> FEATURE:
<223> OTHER INFORMATION: Probe

<400> SEQUENCE: 3
ccaatagctt caacaatt                                                   18
```